(12) United States Patent
Uri et al.

(10) Patent No.: US 8,158,376 B2
(45) Date of Patent: Apr. 17, 2012

(54) BISUBSTRATE FLUORESCENT PROBE BINDING TO PROTEIN KINASES

(75) Inventors: Asko Uri, Tartu (EE); Erki Enkvist, Tartu (EE); Indrek Viil, Tartu (EE); Darja Lavõgina, Tartu (EE); Gerda-Johanna Raidaru, Tartu (EE); Kaido Viht, Tartu (EE)

(73) Assignee: University of Tartu, Tartu (EE)

( * ) Notice: Subject to any disclaimer, the term of this patent is extended or adjusted under 35 U.S.C. 154(b) by 511 days.

(21) Appl. No.: 12/377,839

(22) PCT Filed: Aug. 14, 2007

(86) PCT No.: PCT/EE2007/000015
§ 371 (c)(1),
(2), (4) Date: Feb. 17, 2009

(87) PCT Pub. No.: WO2008/019696
PCT Pub. Date: Feb. 21, 2008

(65) Prior Publication Data
US 2010/0233743 A1    Sep. 16, 2010

(30) Foreign Application Priority Data

Aug. 15, 2006 (EE) .................................. 200600030

(51) Int. Cl.
*C12Q 1/48* (2006.01)
*C07D 473/00* (2006.01)
*C07D 221/18* (2006.01)

(52) U.S. Cl. ............. 435/15; 435/194; 544/277; 546/26

(58) Field of Classification Search .................... 435/15, 435/194; 544/277; 546/26
See application file for complete search history.

(56) References Cited

FOREIGN PATENT DOCUMENTS
WO    WO-00/70029 A1    11/2000

OTHER PUBLICATIONS

Uri et al. Biorg. Med. Chem. Lett. (2002) 12: 2117-2120.*
Loog et al. Biorg. Med. Chem. Lett. (1999) 9: 1447-1452.*
Engh et al. J. Biol. Chem. (1996) 271(42): 26157-23164.*
Eller et al. J. Biochem. (1993) 114: 177-180.*
Ingersoll et al. J. Chem. Ed. (2007) 84(8): 1313-1315.*
Parang et al., "Designing bisubstrate analog inhibitors for protein kinases", Pharmacology & Therapeutics, XP-002459405, vol. 93, No. 2-3, Feb. 2002, pp. 145-157.
Viht et al., "Liquid-Phase Synthesis of a Pegylated Adenosine-Oligoarginine Conjugate, Cell-Permeable Inhibitor of cAMP-Dependent Protein Kinase", Bioorganic & Medicinal Chemistry Letters, XP-002459406, vol. 13, No. 18, Sep. 15, 2003, pp. 3035-3039.
Viht et al., "Fluorometric TLC assay for evaluation of protein kinase inhibitors", Analytical Biochemistry, XP-004817002, vol. 340, No. 1, May 1, 2005; pp. 165-170.
Ricouart et al., "Design of Potent Kinase Inhibitors Using the Bisubstrate Approach", Journal of Medicinal Chemistry, XP-002918324, vol. 34, No. 1, 1991, pp. 73-78.
Viht et al., "Surface-plasmon-resonance-based biosensor with immobilized bisubstrate analog inhibitor for the determination of affinities of ATP—and protein-competitive ligands of cAMP-dependent protein kinase", Analytical Biochemistry, XP-005883095, vol. 362, No. 2, Feb. 13, 2007, pp. 268-277.
Enkvist et al., "Conjugation of Adenosine and Hexa-(D-arginine) Leads to a Nanomolar Bisubstrate-Analog inhibitor of Basophilic Protein Kinases", Journal of Medicinal Chemistry, XP-002465756, Nov. 24, 2006, vol. 49, No. 24, pp. 7150-7159.

* cited by examiner

*Primary Examiner* — Susan Hanley
(74) *Attorney, Agent, or Firm* — Birch, Stewart, Kolasch & Birch, LLP

(57) ABSTRACT

This invention relates to fluorescent probes for identification of compounds binding to protein kinases, for measurement of the affinity of inhibitors of protein kinases, and determination of the active concentration of protein kinases binding to the probe. Bisubstrate-analog character of the probe enables the simultaneous evaluation of inhibitors targeted to both ATP binding site and/or substrate protein/peptide binding domain of the kinase. High affinity of the probe ($K_d$=1.0 nM towards cAMP-dependent protein kinase) affords the application of the enzymes at low concentration which leads to the substantial decrease of the consumption of the kinase. Due to the ability of the conjugates of oligo(D-arginine) with a ATP binding site targeted inhibitors of this invention to bind with high affinity to a wide spectrum of (basophilic) kinases, a single Fluorescent probe is applicable for assessment of inhibitory potency of compounds towards a great number of protein kinases.

16 Claims, 8 Drawing Sheets

BISUBSTRATE FLUORESCENT PROBE BINDING TO PROTEIN KINASES

RELATED APPLICATION

This application is a National Phase of PCT/EE2007/0000151 filed on Aug. 14, 2007, which claims priority under 35 U.S.C. 119(a) to Patent Application No. P200600030 filed in Estonia on Aug. 15, 2006, all of which are hereby expressly incorporated by reference into the present application.

FIELD OF THE INVENTION

The invention concerns a novel fluorescent probe binding to the active site of a protein kinase and its application for screening of compounds and evaluation of inhibitors targeted both to the ATP-binding pocket or/and protein/peptide substrate-binding domain of the kinase, and methods of manufacturing of such probes.

The invention also relates to the screening assay for identifying compounds that bind to and modulate the activity of a wide variety of members of protein kinase super-family. The invention relates to the assay for identification and evaluation of protein kinase inhibitors and determination of the concentration of protein kinases.

BACKGROUND TO THE INVENTION

Protein Kinases and Protein Kinase Inhibitors

Protein kinases (PKs) play a key role in the regulation of protein functions in living cells. It has been estimated that the activity of one third of proteins is regulated through phosphorylation of one or more of serine, theorine and thyrosine residues of the protein. More than 400 human diseases (incl. cancer) have been linked to aberrant protein kinase signaling. This has made PK the second largest drug target (and fastest growing category of drugs in development) after G protein-coupled receptors. [Cohen, Nat. Rev. Drug Discov. 1 (2002) 309; Fischer, Curr. Med. Chem. 11 (2004) 1563]

Protein kinases follow ternary complex kinetic mechanism in which direct transfer of the phosphoryl group from ATP to the protein substrate occurs in the active site. [Adams, Chem. Rev. 101 (2001) 2271]

Three different kind of active site-targeted protein kinase inhibitors are previously known. Firstly, despite serious selectivity problems (all 500 protein kinases and more than 1500 other proteins are able to bind purine nucleotides), and high concentration of competing ATP in the cellular milieu, the main efforts of drug companies have been directed to the development of ATP competitive inhibitors. Imatinib, a specific small molecule inhibitor of the Abl kinase, has become the first successful breakthrough in kinase-targeted cancer therapy.

The second type of active site targeted inhibitors of protein kinases comprise compounds that selectively interfere with protein-protein interactions and block the binding of the substrate protein to the active site of the protein kinase. [Recent reviews: Bogoyevitch et al., Biochim. Biophys. Acta. 1754 (2005) 79; Lawrence, New Design Strategies for Ligands That Target Protein Kinase-Mediated Protein-Protein Interactions.; Pinna, A. L., Cohen, P. T. W. Eds.; 2005; p. 11]

Thirdly, combination of the aforementioned approaches and development of bisubstrate-analog (biligand) inhibitors that simultaneously associate with both ATP and protein binding domains of the dual substrate enzyme has given selective and potent inhibitors of PK. Several strategies of the design of bisubstrate-analog inhibitors have been described. [For a review on the subject, see: Parang et al., Pharmacol. Therap. 93 (2002) 145]. Construction of bisubstrate-analogue (bifunctional) inhibitors could lead to enhanced specificity and potency in protein kinase inhibition. The inhibitor mimics two natural substrates/ligands and associates with two regions of a given kinase simultaneously. Most bisubstrate analogues have been designed to mimic ATP and the acceptor component. The inhibitors of this kind are covalent conjugates between one moiety inhibiting ATP binding and one moiety inhibiting binding of a protein/peptide substrate to the protein kinase. [Ricouart et al., J. Med. Chem. 34 (1991) 73; Medzihradszky et al., J. Am. Chem. Soc. 116 (1994) 9413; patent application describing bisubstrate analog inhibitors of PK: WO0070029, WO0170770, WO03010281, WO2004110337, EE200300187]

One of the present inventors has previously developed bisubstrate-analog inhibitors for protein serine/threonine kinases PKA and PKC with activities in sub-micromolar region. [Loog et al., Bioorg. Med. Chem. Lett., 9 (1999) 1447, Uri et al., Bioorg. Med. Chem. Lett., 12 (2002) 2117, WO0070029, EE200300187]. These inhibitors comprise moieties of analogs of both substrates of protein kinases: ATP binding site targeted adenosine-5'-carboxylic acid (Adc) and the protein substrate domain directed oligo-(L-arginine). The design of the latter fragment was based on the knowledge that phosphorylation sites of the substrates of basophilic protein kinases (cAPK, PKC, Akt/PKB, PKG, etc.) are flanked by regions rich in arginine or/and lysine residues. [Pinna et al., Biochim. Biophys. Acta. 1314 (1996) 191] Two active fragments of the inhibitors were connected via a tether which length was optimized in structure-activity studies.

After the priority date (Aug. 15, 2006) the synthesis and characterization of bisubstrate-analog inhibitors for protein serine/threonine kinases incorporating D-arginine residues that is the subject of the present patent application was described in two published articles by inventors of the present patent application. [Enkvist et al., J. Med, Chem. 49 (2006) 7150; Viht et al., Anal. Biochem., 362 (2007) 268]

Existing Assay Methods

Development of new assay methods for evaluation of protein kinase inhibitors has run in parallel with the increase of importance of effective inhibitors for drug industry. During recent years, flexible fluorometric kinase assay methods have substituted problematic (e.g., personal risks, environmental hazards, short half-lives of 32P- and 33P-labeled compounds, long exposure times) radiometric methods. Fluorescent methods can be spatially and temporally more focused than radioactive methods, and as such, they are more suitable for application in high-throughput screening (HTS) assays. [Olive, Expert Rev Proteomics. 1 (2004) 327]

Great majority of evaluations of kinase inhibitors is performed in the form of kinetic studies and the new, potential inhibitors are screened and characterized on the basis of their retarding effect on the rate of substrate (peptide or protein) phosphorylation reaction catalyzed by the kinase. In the case of radioactive methods the product of the phosphorylation reaction that is covalently labeled with radioactive phosphor isotope is separated from radioactive ATP and quantified. The application of labor-intensive separation steps and the use of large amounts of radioactivity make these methods problematic for high throughput assays.

Kinetic methods where the amount of the product of the phosphorylation reaction is established by its competition with a fluorescent binder for an antibody (a phosphopeptide formed in a kinase reaction displaces a fluorescently-labeled phosphopeptide from a phospho-specific antibody) or other phosphopeptide binding macromolecule (Immobilized Metal Assay for Phosphochemicals, IMAP) is another class of assays in active use. [e.g., WO9818956]. In this case the change in the fluorescence anisotropy resulting from the displacement of the fluorescent binder from its complex with the antibody is usually measured. Although these methods suit better for HTS assays, they still require an effective substrate, fluorescent binder and high-affinity antibody or other phosphor-binding macromolecule for the method. Large number of measurements has to be performed to characterize the inhibitory compounds with comparable $K_i$ values.

Alternatively, kinase inhibitors may be detected by direct or indirect measurement of the binding of the inhibitor to the kinase. Some small-molecule inhibitors can be conjugated to a fluorescent dye without loosing their binding affinity to kinase. The kinase-bound labeled inhibitor can then be displaced by competitive kinase inhibitors and the change in fluorescent characteristics measured. This interaction therefore forms the basis for a competitive binding assay of kinase inhibitors where no knowledge of the substrate or an antibody to the phosphorylated kinase substrate is required. Several papers and patent applications describe the use of fluorescent probes for determination of the binding characteristics of protein kinase inhibitors. [e.g., Chen et al., 268 (1993) 15812, WO2005/033330]

Limitations of Current Binding Assays

Fluorescent probes with micromolar affinity towards cAPK were disclosed by Chen et al. [Chen et al., 268 (1993) 15812] These ATP-competitive probes have complicated emission characteristics that originate from the fluorescence of both the fluorescent dye and bisindolylmaleimide ligand. Low (micromolar) affinity and complex fluorescence spectrum make it difficult to use these fluorescent conjugates as probes for binding assays. [WO9906590] Other ATP competitive fluorescent probes have been described in literature. [e.g., WO2005/033330]

A fluorescent probe targeted to the protein/peptide substrate binding domain of the cAMP-dependent protein kinase (cAPK), fluorescein-labeled 20 amino acid residues-containing sequence of protein kinase heat stable inhibitor protein PKI (PKI 5-24), was shown to bind to cARK with micromolar affinity ($K_d$=1.6 µM) in a fluorescence polarization assay. [Shneider et al., Org. Lett. 7 (2005) 1695] Low binding affinity of the probe prevents its application for the determination of the binding constants of the protein/peptide substrate-binding domain targeted inhibitors.

The main limitations of the binding assays that have been disclosed so far are the following:
  A. Fluorescent probes available have low affinity (usually micromolar or submicromolar) towards protein kinases that leads to substantially higher consumption of kinases when using these methods if compared to kinetic assays, and to the impossibility of the application of the probes for determination of exact binding characteristics of high-affinity inhibitors;
  B. Fluorescent probes available are active to a single kinase or a small family of kinases that makes it impossible to use a single probe for generic characterization of inhibitors with multiple kinases;
  C. All fluorescent probes available thus far enable the testing of compounds binding to either ATP or protein/peptide substrate binding site and as such differently from kinetic methods do not permit simultaneous screening of ATP and protein-peptide substrate binding site-targeted inhibitors.

To our knowledge, prior art published by other groups most related to the current invention is described in the patent application WO2005/033330 "Fluorescent probes for use in protein kinase inhibitor binding assay". This invention describes a fluorescent probe with affinity in high nanomolar range ($K_d$=161 nM) which leads to the need for high concentration of the kinase in the assay format (200 nM STK12 kinase was used in the disclosed Example). Requested kinase concentration, arising from the $K_d$ value of the fluorescent probe, is a hundred-fold higher than the kinase concentration usually applied for kinetic measurements (ca 1 nM concentration of the enzyme is often used in kinetic assays). This leads to substantial increase of the cost of the assay. Due to sub-micromolar dissociation constant of the probe it cannot be used for determination of binding constants of inhibitors with nanomolar affinity [Fluorescence Polarization Technical Resource Guide THIRD EDITION 2004, Invitrogen Corporation. Chapter 7]

The probe disclosed in WO2005/033330 is targeted to the ATP binding site of the kinase and as such the application of the probe for screening of PK inhibitors neglects the inhibitors targeted to the protein/peptide binding domain of the kinase. Furthermore, the fluorescent probe disclosed in WO2005/033330 is applicable for testing of inhibitors of a specific kinase (STK12 and close analogs).

Benefits of the Presented Invention

The invention described in current patent application overcomes limitations of all known fluorescent probes and is applicable in competitive displacement assays for identification and characterization of inhibitors of many protein kinases and determination of the concentration of the protein kinase. If compared to the probes from previous inventions, the Fluorescent probe of the present invention has very high affinity ($K_d \leq 1$ nM) and can be used for testing of inhibitors of a variety of protein kinases targeted to both ATP and/or protein substrate binding sites.

SUMMARY OF THE INVENTION

This invention relates to fluorescent probes for identification of compounds binding to protein kinases, for measurement of the affinity of inhibitors of protein kinases, and determination of the active concentration of protein kinases binding to the probe. Bisubstrate-analog character of the probe enables the simultaneous evaluation of inhibitors targeted to both ATP binding site and/or substrate protein/peptide binding domain of the kinase.

High affinity of the probe ($K_d$=1.0 nM towards cAPK) affords the application of the enzymes at very low concentration ($\leq 1$ nM) which leads to the substantial decrease of the consumption of the kinase. The probe is applicable for exact determination of binding constants for inhibitors with nanomolar and micromolar affinity. Due to the ability of the conjugates of oligo(D-arginine) with a ATP binding site targeted inhibitors of this invention to bind with high affinity to a wide spectrum of (basophilic) kinases, a single Fluorescent probe is applicable to a number of protein kinases.

$$A = A_f + (A_b - A_f) \times \frac{(L_T + K_d + R_T) - \sqrt{(L_T + K_d + R_T)^2 - 4 L_T R_T}}{2 L_T} \quad (A)$$

A is measured anisotropy; $A_f$ is the anisotropy of free ARC-TAMRA; $A_b$ is the anisotropy of bound ARC-TAMRA; $L_T$ is the concentration of ARC-TAMRA added, 10 nM; $R_T$ is the concentration of the total kinase (cAPK Cα).

Figure 1:
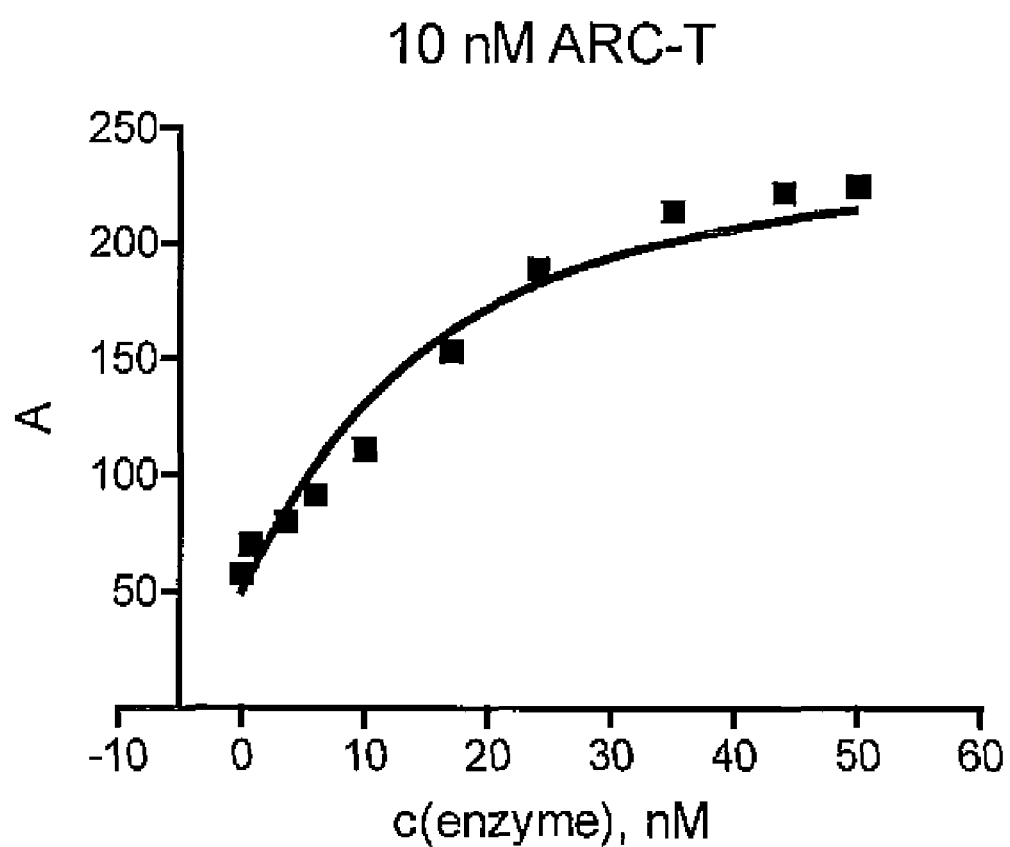
FIG. 1. Titration of the fluorescent probe ARC-TAMRA (10 nM) with cAPK Cα (fluorescence spectrometer LS 55 (Perkin Elmer) with 0.5 ml quartz cell). $K_d$=1.1 nM was calculated with the application of nonlinear regression analysis to the relationship.
Figure 2:
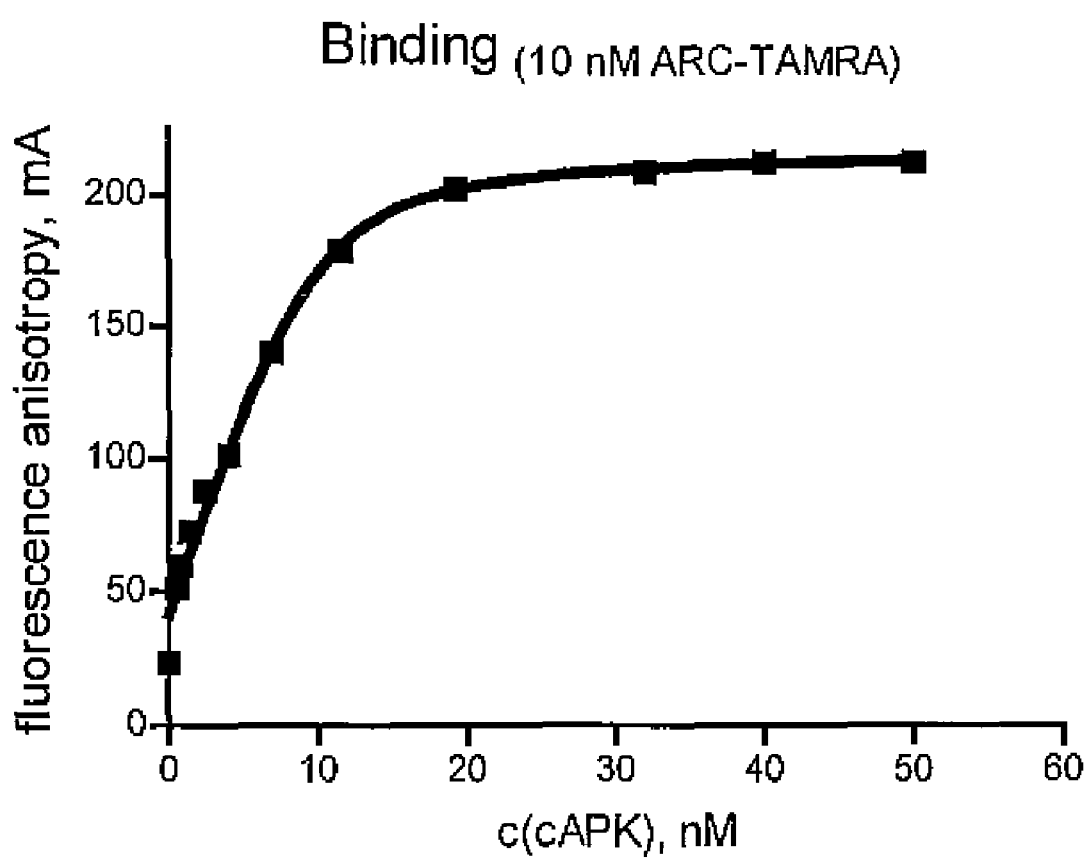

FIG. 2. Titration of ARC-TAMRA (2 nM and 10 nM) with cAPK Cα (fluorescence spectrometer LS 55 (Perkin Elmer) with 0.5 ml quartz cell). $K_d$ values of 1.1 nM and 0.94 nM were calculated for 2 nM and 10 nM of ARC-TAMRA, respectively from the relationship (A) (FIG. 1).

Figure 3:
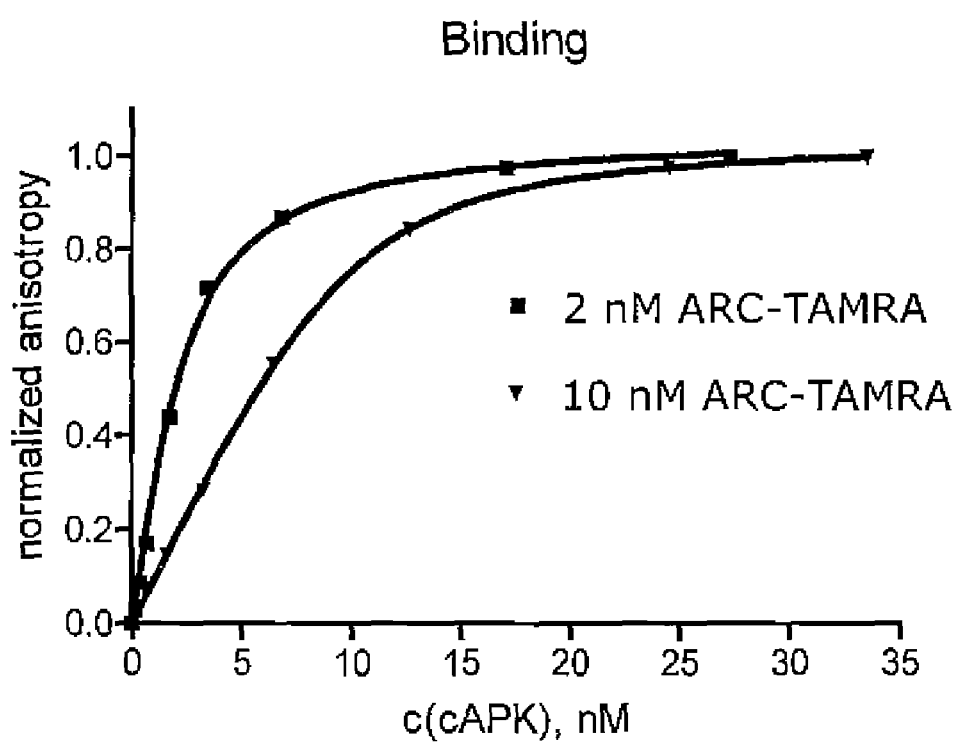

FIG. 3. Determination of the concentration of the active kinase (fluorescence spectrometer LS 55 (Perkin Elmer) with 0.5 ml quartz cell).

The fraction of the active (binding) form of the kinase in solution, k=0.317, was calculated by the application of non-linear regression analysis to the relationship:

$$A = A_f + (A_b - A_f) \frac{L_t + K_d + k \cdot R_t - \sqrt{(L_t + K_d + k \cdot R_t)^2 - 4 \cdot L_t \cdot k \cdot R_t}}{2 \cdot L_t} \quad (B)$$

A is the measured anisotropy; $A_f$ is the anisotropy of free ARC-TAMRA; $A_b$ is the anisotropy of bound ARC-TAMRA; $L_T$ is the concentration of ARC-TAMRA added, 10 nM; $R_T$ is the total (nominal) concentration of kinase (cAPK Cα); $K_d$ is the dissociation constant of the reaction between ARC-TAMRA and cAPK Cα ($K_d$=1.0 nM).

Figure 4:
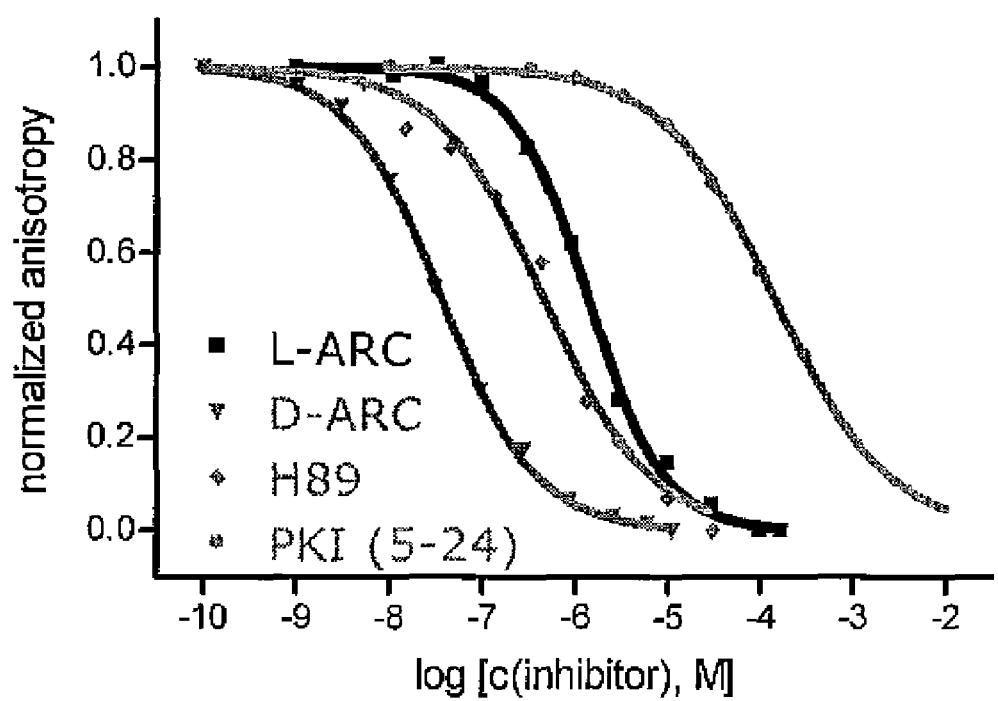

FIG. 4. Dependence of anisotropy (normalized values) on the concentration of inhibitors H89; PKI [inhibitory peptide PKI (5-24)], ARC [AdcAhx(L-Arg)$_6$-NH$_2$], and D-ARC [AdcAhx(D-Arg)$_6$-NH$_2$]. Assay conditions: 10 nM of ARC-TAMRA and 10 nM of kinase (cAPK Cα), fluorescence spectrometer LS 55 (Perkin Elmer) with 0.5 ml quartz cell. The $K_d$ value of 1.0 nM was used for ARC-TAMRA.

The obtained inhibitory characteristics for inhibitors were as follows:

| Inhibitor | IC$_{50}$ | K$_i$ |
|---|---|---|
| L-ARC | 1.3 μM | 110 nM |
| D-ARC | 35 nM | 2.5 nM |
| H89 | 180 nM | 15 nM |
| PKI (5-24) | 140 μM | 12 μM |

Figure 5:
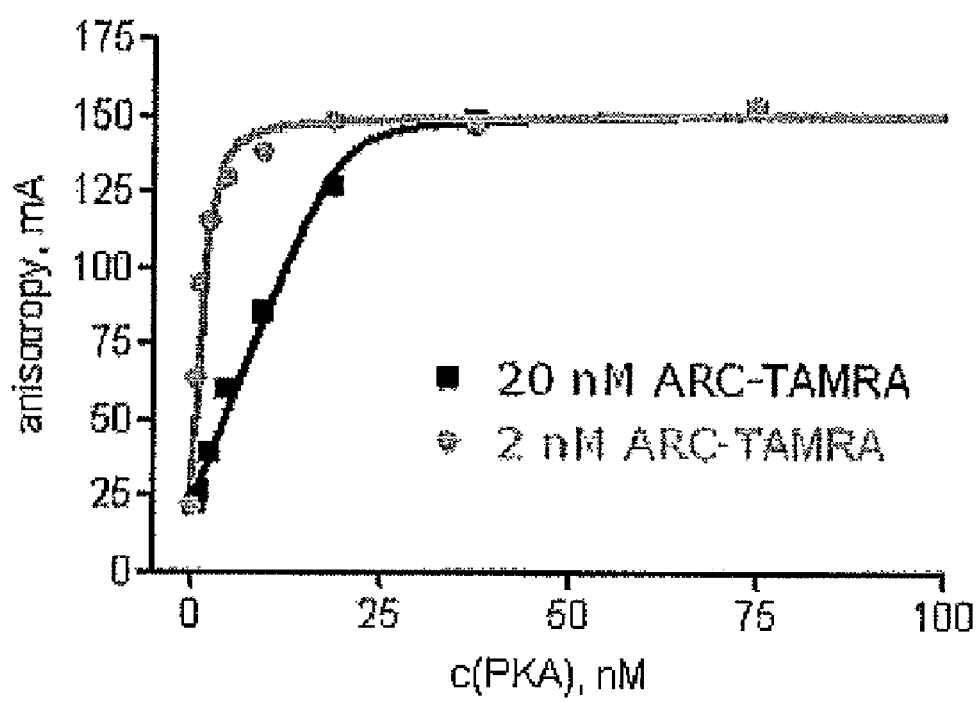

FIG. 5. Titration of ARC-TAMRA (2 nM and 20 nM) with cAPK Cα (fluorescence plate reader PHERAstar (BMG LABTECH), Corning 384 well Low Volume NBS microplates (30 μl reaction volume)). $K_d$ value of 0.4 nM was calculated from the relationship (A) (FIG. 1).

Figure 6:
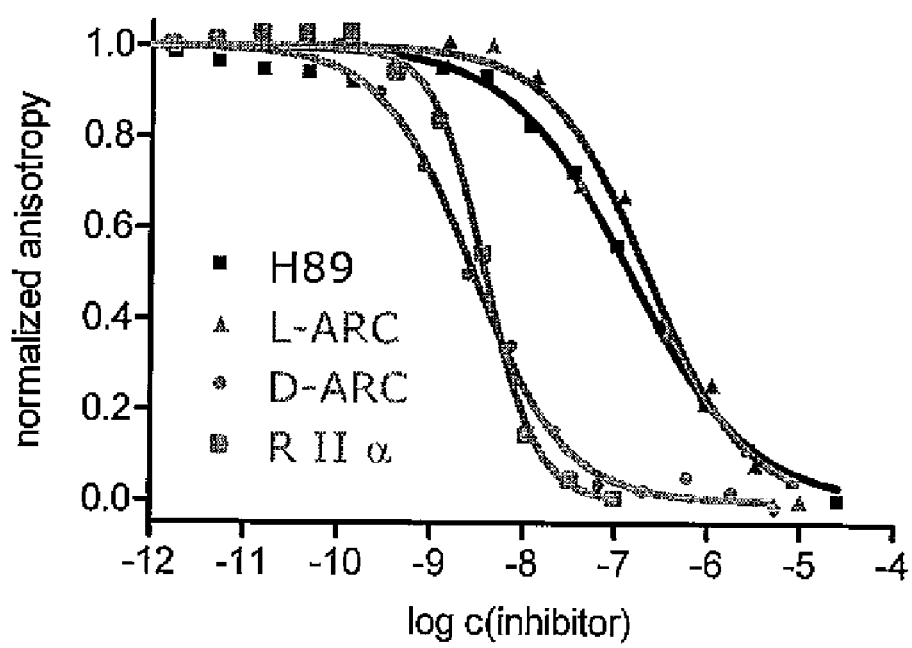

FIG. 6. Dependence of anisotropy (normalized values) on the concentration of inhibitors H89; ARC [AdcAhx(L-Arg)$_6$-NH$_2$], D-ARC [AdcAhx(D-Arg)$_6$-NH$_2$], and the regulatory subunit of cAMP-dependent protein kinase RIIα. Assay conditions: 2 nM of ARC-TAMRA and 3 nM of kinase (cAPK Cα), fluorescence plate reader PHERAstar (BMG LABTECH). The $K_d$ value of 0.4 nM was used for ARC-TAMRA. K$_j$ values of 21 nM (AdcAhx(L-Arg)$_6$-NH$_2$), 13 nM (H89), 1.1 nM (AdcAhx(D-Arg)$_6$-NH$_2$), and 0.5 nM (RIIa) were obtained.

Figure 7:
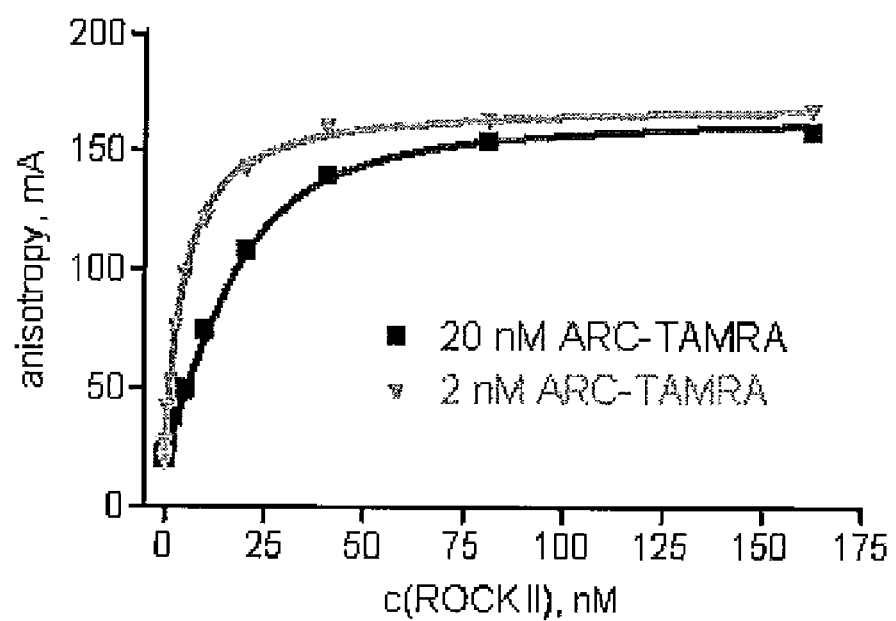

FIG. 7. Titration of ARC-TAMRA (2 nM and 20 nM) with Rho-associated kinase ROCK II (fluorescence plate reader PHERAstar, BMG LABTECH). $K_d$ value of 4 nM was calculated for ARC-TAMRA-ROCK II complex according to the relationship (A) (FIG. 1).

Figure 8:
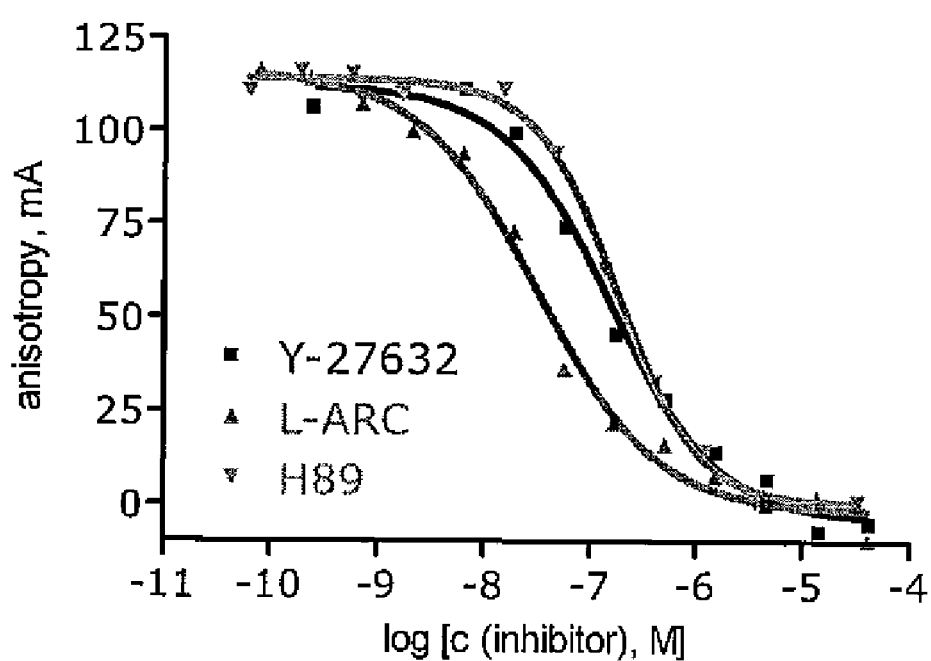

FIG. 8. Dependence of anisotropy on the concentration of inhibitors H89, Y-27632, and ARC [AdcAhx(L-Arg)$_6$-NH$_2$]. Assay conditions: 2 nM of ARC-TAMRA and 15 nM ROCK II, fluorescence plate reader PHERAstar (BMG LABTECH). The $K_d$ value of 4.0 nM was used for ARC-TAMRA. Ki values of 45 nM (H89), 40 nM (Y-27632) and 5 nM (AdcAhx (L-Arg)$_6$-NH$_2$) were obtained.

DETAILED DESCRIPTION OF INVENTION

This invention relates to fluorescent probes for the identification of compounds binding to protein kinases, for measurement of the affinity of inhibitors towards protein kinases and determination of the active concentration of protein kinases binding to the probe. Bisubstrate-analog character of the probes enables the evaluation of inhibitors targeted to both ATP binding site and protein/peptide substrate binding domain of the kinase. The fluorescent probe of this invention has very high affinity towards the kinase ($K_d$=1.0 nM) which enables the application of low concentrations of kinases in assays and determination of binding constants for inhibitors with high (low nanomolar) affinity. Displacement of the fluorescent probe by an inhibitor can be used for the determination of the values of dissociation constants $K_d$ for the reaction of the inhibitor with many protein kinases.

Fluorescent Probe

The first embodiment of the invention is a fluorescent probe with the general formula (I):

(X—Y—Z)-L-F     (I), wherein X—Y—Z is a bisubstrate-analog inhibitor of a protein kinase, in which X is targeted to the ATP-binding pocket of a kinase, Z binds to the protein/peptide-binding domain of the kinase, Y is a tether that connects X and Z and permits simultaneous binding of X and Z to the active site of the kinase; F is a fluorescent dye which optical characteristics are changed in the course of the binding of (X—Y—Z)-L-F to the kinase; L is a linker between the bisubstrate-analog inhibitor XYZ and fluorescent label F.

The presently preferred fluorescent probe for the application in the binding assay has the structure:

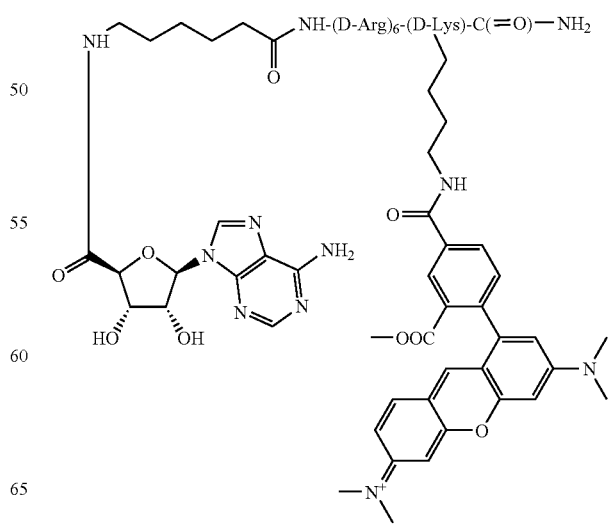

AdcAhx(D-Arg)$_6$-D-Lys(5-TAMRA)-C(O)NH$_2$, ARC-TAMRA

The probe, ARC-TAMRA, has high affinity (K$_d$=1.0 nM; FIGS. 1 and 2, Example 4) towards the catalytic subunit of cAMP-dependent protein kinase (cAPK Cα) and it was displaced from its complex with the kinase by ATP-competitive inhibitor H89, protein substrate competitive inhibitor peptide PKI (5-24), and bisubstrate inhibitor AdcAhx(D-Arg)$_6$-NH$_2$ (Example 5, FIG. 3). Thus, the fluorescent probe of the present invention ARC-TAMRA is the first high-affinity probe disclosed that can be used to measure simultaneously the affinity of inhibitors binding to ATP and protein substrate binding sites of the kinase. The bisubstrate (biligand) character of the probe AdcAhx(D-Arg)$_6$-D-Lys(5-TAMRA)-C(O)NH$_2$ is proved with its displacement from the complex with the kinase by both ATP-binding site targeted inhibitor H89 and protein/peptide substrate binding site targeted inhibitor PKI (5-24), and also by very high affinity of the fluorescent probe.

The inhibitory part of the probe AdcAhx(D-Arg)$_6$-NH$_2$ has high inhibitory potency to many protein kinases (Table 3). As such the fluorescent probe has the potential for application in assays concerning many basophilic protein kinases. Selective inhibition of basophilic kinaseses by AdcAhx(D-Arg)$_6$-NH$_2$ (Table 3) is another demonstration of the bisubstrate nature of the inhibitors of the present invention.

5-TAMRA, 5-carboxytetramethylrhodamine, is a good fluorescent label to be used in fluorescence polarization assays, as it contains the dye as a single-position isomer, the probe is exited at long wavelength, it has high brightness and great photostability.

Other fluorescent labels are suitable for the application as the moiety F of the fluorescent probe (X—Y—Z)-L-F. These fluorescent dyes are well known to the people skilled in the art. Principles for the choice of fluorescent labels are Disclosed in [Polarization Technical Resource Guide • THIRD EDITION 2004 Invitrogen Corporation, USA, the Invitrogen.com/panveral website. Many such labels are described in the Handbook: [The Handbook—A Guide to Fluorescent Probes and Labeling Technologies Web Edition of The Handbook, Tenth Edition 2006 Invitrogen Corporation]

Usually fluorescence labels with higher brightness (brightness of a fluorochrome is proportional to the product of its extinction coefficient and its quantum efficiency), longer excitation and emission wavelengths, and greater photostability are preferred, but the choice of the label depends on the analytical instrument used for the assay and special analytical situation. Other fluorescent dyes that may be useful in the present invention include fluorescein and fluorescein derivatives, rhodamine and rhodamine derivatives, and many other fluorescent labels that are produced and sold by different companies. Fluorescent probes of the structure (X—Y—Z)-L-F incorporating as F mineral fluorescent labels, e.g., quantum dots, may be useful for special applications.

The aim of the linker L in the structure of the fluorescent probe (X—Y—Z)-L-F is the positioning of the fluorescent label F in the position where the group F causes minimal hindrance to the binding of the bisubstrate inhibitor X—Y—Z to the kinase. In the preferred fluorescent probe AdcAhx(D-Arg)$_6$-D-Lys(5-TAMRA)-C(O)NH$_2$ D-lysine stands for the linker L but in the case of other probes the linker may be a C$_1$-C$_{20}$ alkylene group, a C$_1$-C$_{20}$ alkenylene group, a C$_1$-C$_{20}$ alkynylene group, wherein one or more of the CH$_2$ groups present in the C$_1$-C$_{20}$ alkylene group, C$_1$-C$_{20}$ alkenylene group, C$_1$-C$_{20}$ alkynylene group is optionally replaced with —O—, —C(O)—, —C(O)N—, —S—, —S(O)—, —SO$_2$—, —N(R)—; R is H or C$_{1-6}$ alkyl. In the case of some probes L may be omitted.

In the examples of the present invention the fluorescent dye F is connected via linker L to the moiety Z of bisubstrate inhibitor X—Y—Z, but L may also be attached to any of the X, Y and Z moieties at various locations.

As it will be shown in later parts of the invention other types of bisubstrate inhibitors may form the active ingredient X—Y—Z of the fluorescent probe. An example of another fluorescent probe structure is the compound where Hidaka's ATP competitive PK inhibitor H9 is conjugated with hexa(D-arginine) peptide via flexible hexanoic acid tether. The compound 26H9-(CH$_2$)$_5$C(O)(D-Arg)$_6$-NH$_2$ with very high inhibitory potency (IC$_{50}$=5.3 nM; K$_i$=1-2 nM; Example 2, Table 2) was connected through D-lysine linker to the fluorescent label 5-TAMRA to obtain high-affinity fluorescent probe of the present invention
H9-Hex(D-Arg)$_6$-D-Lys(5-TAMRA)-C(O)NH$_2$:

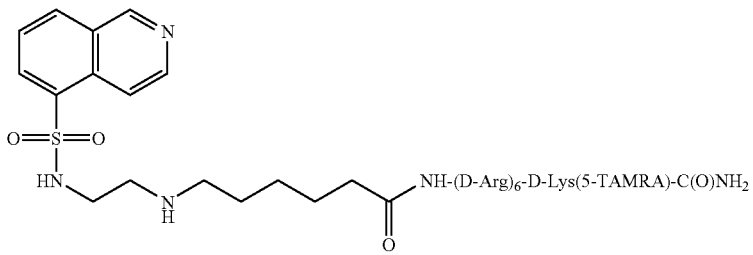

As it will be described further in Example 2H9-Hex(D-Arg)$_6$NH$_2$ (Compound 26) has very high affinity towards the kinase cAPK. Inhibitory selectivities of bisubstrate inhibitors AdcAhx(D-Arg)$_6$-NH$_2$ and H9-Hex(D-Arg)$_6$NH$_2$ towards basophilic kinases are somewhat different (Example 3) and the derived fluorescent probes AdcAhx(D-Arg)$_6$-D-Lys(5-TAMRA)-C(O)NH$_2$ and H9-Hex(D-Arg)$_6$-D-Lys(5-TAMRA)-C(O)NH$_2$ (synthesis of both probes id described in Example 1) may find application in different assay formats.

Although the preferred method of the invention is to use the fluorescent probe with fluorescence polarization measurement, an environmentally sensitive fluorescent probe is another choice of the present invention: change in fluorescent intensity as the result of the binding of the probe to the kinase would be measured rather than the change in the fluorescence polarization. A preferred fluorescent probe for these measurements is AdcAhx(D-Arg)$_6$-D-Lys(NBD)-NH$_2$.

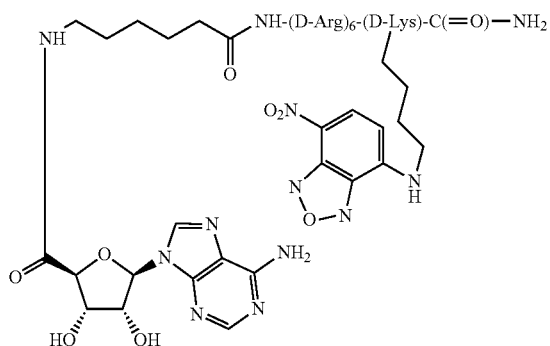

AdcAhx(D-Arg)$_6$-D-Lys(NBD)-NH$_2$

The probe contains NBD (7-Nitrobenz-2-Oxa-1,3-Diazole) dye which fluorescence intensity is strongly dependent on environment. The probe has very high affinity towards cAPK ($K_d$ ca 1 nM). The synthesis of the fluorescent probe AdcAhx(D-Arg)$_6$-D-Lys(NBD)-NH$_2$ is described in Example 1.

People skilled in the art know that there are other possibilities (in addition to fluorescence polarization and fluorescence intensity measurements) to measure the change in fluorescence of a probe as a result of its association with a kinase. The methods like fluorescence correlation spectroscopy, fluorescence resonance energy transfer (FRET), fluorescence lifetime, photo-bleaching and photo-activation, fluorescence intensity distribution analysis and their combinations can be used for the monitoring the equilibrium of the reaction between a fluorescent probe and a protein. These methods are well characterized in literature [e.g., White et al. Adv. Drug Deliv. Rev. 57 (2005) 17] and may find application in kinase association studies connected to the fluorescent probes disclosed in the present inventors. The probes of the present invention can be used with classical fluorescence techniques and confocal single-molecule techniques in single- and multi-parameter imaging formats [Tinnefeld et al., Angew. Chem. Int. Ed. 44 (2005) 2642].

Authors of the present invention have shown that adenosine—oligoarginine conjugates are cell membrane permeable [Uri et al., Bioorg. Med. Chem. Lett. 12 (2002) 2117], therefore the fluorescent probes of the present invention are applicable in experiments with live cells, tissues and organisms. Preferred embodiments of the present invention, fluorescent probes AdcAhx(D-Arg)$_6$-D-Lys(5-TAMRA)-C(O)NH$_2$, H9-Hex(D-Arg)$_6$-D-Lys(5-TAMRA)-C(O)NH$_2$, AdcAhx(D-Arg)$_6$-D-Lys(NBD)-NH$_2$ contain D-arginines, differently from previously disclosed bisubstrate inhibitors which incorporate L-isomers of amino acids. As such these probes are persistent towards enzymatic degradation. [Elmquist, Biol. Chem. 384 (2003) 387] and well suited for applications in biological systems. In biological systems fluorescent probes of the present invention could be used together with kinases fused to fluorescent proteins for dual color imaging and protein-inhibitor interaction studies based on measurement of fluorescence resonance energy transfer (FRET).

The Fluorescence Polarization Assay

The preferred assay method for the application of the fluorescent probes of the present invention is fluorescence polarization or fluorescence anisotropy. Both terms are used synonymously to describe molecular interactions in solution. [Fluorescence Polarization Technical Resource Guide • Analysis of FP Binding Data Invitrogen Corporation •USA•, the Invitrogen.com/panveral website.

This technique measures the change in rotational speed of a ligand during its excited lifetime upon binding to its receptor.

Fluorescence polarization assays are homogeneous and as such they do not require separation steps like chromatography, filtration, centrifugation, precipitation or electrophoresis. Due to the ratiometric nature of the assay fluorescence polarization is well suited to assay miniaturization, and the assays can be performed with equal success in a cuvette of a fluorescence spectrometer and in low µl volumes in wells of 1536-well microtiter plates with a stable plate reader with a fluorescence polarization detector. In the embodiments of the present invention fluorescence spectrometer LS 55 (Perkin Elmer) with 0.5 ml quartz cell or fluorescence plate reader PHERAstar (BMG LABTECH) with Corning 384 well Low Volume NBS microplates (30 µl reaction volume) were used for assays.

In the experimental setup used here a fluorescence polarization signal is greatly increased when fluorophore is slowed down drastically in its rotational speed. This occurs upon binding of a small fluorescently labelled probe of the present invention to significantly larger molecule of the target protein kinase. The degree of polarization is determined by measuring the fluorescence intensities of parallel and perpendicular emitted light with respect to the plane of linearly polarized excitation light. The preferred embodiment of the Fluorescent probe of the present invention ARC-TAMRA, AdcAhx(D-Arg)$_6$-D-Lys(5-TAMRA)-C(O)NH$_2$, has MW of 1869 and the MW of the kinase, cAPK Cα, is ca 40000. This leads to big differences in the anisotropy values of the solution of free ARC-TAMRA ($A_f$=40 mA) and the solution of the complexed with the kinase fluorescent probe ARC TAMRA ($A_b$=240 mA).

Due to mathematical simplicity, anisotropy values are preferred because it is easier to deconvolute anisotropy values into component values than it is with polarization values.

Fluorescent probe ARC-TAMRA involved in binding events exist in a mixture of only two states: bound or free. With only two species, the anisotropy additivity equation has the shape:

$$A = F_f A_f + F_b A_b,$$

where
Ff+Fb=1;
A=observed anisotropy value
$F_f$=fraction of fluorescent ligand that is free
$F_b$=fraction of fluorescent ligand that is bound
$A_f$=anisotropy of the free fluorescent ligand
$A_b$=anisotropy of the bound fluorescent ligand The top and bottom plateaus of the semi-log equilibrium binding isotherm (anisotropy vs. Log total receptor concentration) define the anisotropy of the free and bound states, Af and Ab. With the observed anisotropy, A, we can calculate the fraction of Bound and Free fluorescent ligand for a given anisotropy value.

The change in fluorescence anisotropy was plotted against the kinase concentration [cAPK Cα]. The data were fitted to the equation:

$$A = A_f + (A_b - A_f) \frac{L_t + K_d + R_t - \sqrt{(L_t + K_d + R_t)^2 - 4 \cdot L_t \cdot R_t}}{2 \cdot L_t}$$

where, A is measured anisotropy; $A_f$ is the anisotropy of free ARC-TAMRA; $A_b$ is the anisotropy of bound ARC-TAMRA;

$L_T$ is the concentration of ARC-TAMRA added; $R_T$ is the total concentration of active kinase (cAPK Cα).

Characterization of the fluorescent probe ARC-TAMRA in binding experiments with the catalytic subunit of cAMP-dependent protein kinase is characterized in Example 4 and FIGS. 1 and 2. Kd of 1.0 nM was determined for the fluorescent probe ARC-TAMRA in these assays.

Competition Experiments

The present invention embodies an assay in which the binding characteristics of the test compounds are determined on the basis of their ability to displace the fluorescent probe from its complex with the kinase in a fluorescence polarization assay. This is described in Example 5 and shown on FIG. 3.

By virtue of the bisubstrate (biligand) character of the fluorescent probe of the present invention it is displaced from the complex with the protein kinase with both ATP binding site targeted inhibitors and protein substrate binding site targeted inhibitors. As it has been shown in FIG. 3 three different types of inhibitors are able to displace the fluorescent probe ARC-TAMRA from its complex with the kinase cAPK Cα:
  a) ATP competitive inhibitor H89;
  b) Protein substrate competitive inhibitor PKI (5-24);
  c) Bisubstrate-analog inhibitors AdcAhx(L-Arg)$_6$-NH$_2$ and AdcAhx(D-Arg)$_6$-NH$_2$ The obtained result (Example 5) reveals that the fluorescent probe of the present invention can be used for evaluation of compounds binding to different binding pockets of the active site of the kinase. Thus, the displacement method of the present invention catches up with kinetic methods in detecting both types of inhibitors in a single assay. This has not been previously possible with fluorescent probes based on ATP competitive or protein substrate competitive inhibitors.

The high affinity of the fluorescent probe of the present invention ($K_d$=1.0 nM) makes it possible to characterize the high-affinity inhibitors H89 ($K_d$=15 nM) and AdcAhx(D-Arg)$_6$-NH$_2$ ($K_d$=2.5 nM). This had not been possible with fluorescent probes having affinity in micromolar or submicromolar region (e.g., the fluorescent probe of the patent application WO2005/033330 has $K_d$ of 140 nM and it cannot be used for the determination of binding constants for inhibitors with low nanomolar affinity).

Also, the high affinity of the fluorescent probe ARC-TAMRA ($K_d$=1.0 nM) and its good fluorescent characteristics make the probe applicable in high throughput screening formats of the fluorescence polarization assay with 384-well and 1536-well microtiter plates. Modern plate-readers with fluorescence polarization detectors enable the application of the fluorescent probe at sub-nanomolar concentration which lowers the requested concentration of the kinase under 3 nM.

Taking into the account the selectivity profile of the bisubstrate inhibitors of the present invention AdcAhx(D-Arg)$_6$-NH$_2$ and H9-Hex(D-Arg)$_6$NH$_2$ (Table 2) the corresponding fluorescent probes are applicable to characterization of the binding of inhibitors to many kinases with basophilic substrate profile.

Additionally, the potential targets of the fluorescent probes of the present invention are different mutated forms of basophilic protein kinases, truncated forms of kinases inactive states of protein kinases, and pseudokinases.

Determination of the Concentration of the Active Form of the Kinase

Determination of the concentration of the special form of a kinase is of paramount importance for many enzyme applications. In kinetic assays the kinase amount in the assay volume is characterized on the activity basis and the molar concentration of the kinase is often not known. Majority of the methods in use for determination of enzyme concentration (Bradford, Lowry, SDS electrophoresis) give the total concentration of the protein (not the concentration of its active form), are inaccurate and need unacceptably large amounts of the protein for analysis.

The application of the fluorescent probe of the present invention ARC-TAMRA enables a simple procedure for the determination of the concentration of the active (binding to the fluorescent probe) form of the kinase in the sample.

The fraction of the active (binding) form of the kinase in solution, k, was calculated with the application of nonlinear regression analysis to the relationship:

$$A = A_f + (A_b - A_f) \frac{L_t + K_d + k \cdot R_t - \sqrt{(L_t + K_d + k \cdot R_t)^2 - 4 \cdot L_t \cdot k \cdot R_t}}{2 \cdot L_t}$$

where A is the measured anisotropy; $A_f$ is the anisotropy of free ARC-TAMRA; $A_b$ is the anisotropy of bound to the kinase form of ARC-TAMRA; $L_T$ is the concentration of ARC-TAMRA added, 10 nM; $R_T$ is the total concentration of active kinase (cAPK Cα); Kd is the dissociation constant of the reaction between ARC-TAMRA and cAPK Cα (Kd=1.0 nM). The application of the fluorescent probe ARC-TAMRA for the determination of the concentration of cAPK Cα is described in Example 6.

It was established that there was good proportionality between the concentration of the binding protein (as established with the fluorescent probe ARC-TAMRA) and the phosphorylation activity of the solution of catalytic subunit of cAMP-dependent protein kinase. The reduction of kinase activity enzyme samples with time was in accord with the determined amount of kinase associated with ARC-TAMRA.

Optimization of the Structure of Bisubstrate Inhibitor X—Y—Z

To be widely applicable in bioanalytical methods the fluorescent probe should have possibly highest affinity towards its target protein. It has been shown that the higher the affinity of the fluorescent ligand, the wider the range of inhibitor potency that can be resolved [Huang, J. Biomol. Screen. 8 (2003) 34]. The lowest inhibitor $K_i$ value that can be resolved in an FP-based binding assay is approximately equal to the $K_d$ value of the fluorescent probe. Starting from the compound AdcAhx(L-Arg)$_6$ with IC50 of 400 nM [Viht et al., Anal. Biochem. 340 (2005) 165; Loog et al., Bioorg. Med. Chem. Lett. 9 (1999) 1447] modifications in the structure of different moieties of the conjugates were performed. Flexible and productive solid phase synthetic methods were developed for the preparation of conjugates of oligoarginine peptides with adenine, adenosine, adenosine-5'-carboxylic acid (Adc), and 5-isoquinolinesulfonic acid for structure-activity studies (Schemes 1-4). Different combinations of fragments were incorporated into conjugates and the novel compounds were tested as inhibitors of cAPK (cAMP-dependent protein kinase).

New Synthetic Methods: Synthesis of Fluorescent Probes and Bisubstrate Inhibitors for SAR Studies The synthesis of the first class of compounds containing Adc (2-8, Scheme 1) was performed with the application of Rink amide resin instead of Wang resin. The structures of tether and peptide components were varied. It was decided to preserve the optimal towards cAPK length of the linker corresponding to that of 6-aminohexanoic acid (equivalent to seven chemical bonds) between the nucleoside and peptide moieties. The optimal length of the tether may be different for other basophilic kinases. Additionally, the tether may contain different heteroatoms and the simple hydrocarbon chain may be substituted with more complicate straight or branched linking units.

The diversity of the structure of the peptide part of the conjugates was achieved by the variation of length and chirality of oligoarginine chain, as represented by peptide moieties of $(L-Arg)_4-NH_2$ (2), $(L-Arg)_6-NH_2$ (3), $(D-Arg)_4-NH_2$ (4) and $(D-Arg)_6-NH_2$ (5).

The second group of compounds contained adenosine and 5'-amino-5'-deoxyadenosine derivatives (Scheme 2). The reaction of 4-nitrophenyl chloroformate with 2,3'-isopropylidene adenosine resulted in the activated carbonate, which gave adenosine-5'-urethanes in the reaction with amines. The length of the linker between nucleoside and peptide moieties was varied. Peptides containing a free amine-group near the C-terminus (e.g., the side chain of lysine or a diamine linker) were prepared on solid phase, cleaved and purified by HPLC.

A special class of biligand inhibitors deprived of ribose moiety, conjugates of adenine and oligoarginine, was synthesized by connecting adenine at C8 or N9 position to a peptide via a linker chain. Precursors of these molecules containing a linker with a free carboxylate group were synthesized in solution. Coupling of the precursors with the resin-bound peptides resulted in conjugates with peptides after cleavage and deprotection with TFA (Scheme 3).

Conjugates of isoquinolinesulfonamide and oligoarginine were synthesized to compare their activity and selectivity to those of analogous adenosine-containing compounds. If compared to the previously synthesised isoquinolinesulfonyl peptides [Ricouart et al., J. Med. Chem. 34 (1991) 73], several changes were introduced into the structures and the synthesis was carried out on solid-phase with the application of Fmoc-peptide and peptoid chemistry procedures. The use of Rink amide resin excluded the presence of negatively charged C-terminal carboxylate group and resulted in products in the form of their C-terminal amides. The conventional Fmoc-peptide chemistry allowed the circumvention of the harsh HF treatment in the final step of Boc-chemistry procedures. The (β-Ala)-Ser linker of previous conjugates was replaced with 6-aminohexanoic acid, which eliminated potentially phosphorylatable serine residue, removed unnecessary chiral centre and simplified the overall synthetic procedure. Resin-bound oligoarginine peptides were acylated at N-terminus with 6-bromohexanoic acid and the following reaction with 5-isoquinolinesulfonyl ethylenediamine and cleavage with TFA led to the 5-isoquinolinesulfonyl ethylenediamine containing conjugate (Scheme 4).

A special embodiment of the present patent application is the group of bisubstrate-analog inhibitors incorporating D-arginine-rich peptides. The high affinity of that kind of conjugates towards cAPK (Table 2) and many other basophilic protein kinases (Table 3) was not known previously. This result is surprising by virtue of the fact that cAPK has a strong requirement for L-configuration both at the phosphorylatable serine residue as well as at the N-terminal arginine residues of the substrate. [Eller, Biochem. Int. 25 (1991) 453] High binding energy may result from beneficial positioning of structurally flexible interacting partners, bisubstrate inhibitor and the kinase, in their complex. Introduction of arginine residues into ARC in the form of their D-configuration converts the peptide motif into retro-inverso counterpart of the C-terminally appended oligo(L-arginine) peptide.

Retro-inverso peptide can be regarded as a derivative of a normal peptide in which the relative amino acid side chain topology is maintained, while the backbone termini and direction of the peptide bonds are reversed. This may lead to substantial synergism of the binding energy of the bisubstrate inhibitor if compared to the sum of the binding energies of its constituents, single-site directed inhibitors. Further specification of the interaction mechanism will be possible after solving the crystal structures of the complexes of these inhibitors with protein kinases.

Using the methods described above, one skilled in the art could readily prepare various bisubstrate analog inhibitors for structure-activity studies. Other building blocks (e.g., purine and pyrimidine nucleosides, bisindolylmaleimides, isoquinolines, staurosporines, balanol, etc.) with affinity towards the kinase under investigation can be introduced into the X moiety of the conjugates X—Y—Z and the new conjugates tested for activity. Likewise, the structure of the peptide part Z and the structure of the tether part Y of the bisubstrate inhibitors X—Y—Z could be further optimized to achieve conjugates with the highest affinity towards a special kinase.

The optimal structure of the organic tether (Y) may vary between different protein kinases and is also dependent on the selection of X and Z. Y should be selected among groups providing a chain comprising from 1-50 atoms, for instance 1-30 atoms, such as 1-18 atoms. In addition to the chain as such there may be groups projecting from the chain. The chain may comprise one or more groups selected from amides (—CONR'—, where R' is selected from the side groups present in amino acids), amines (—NR"—, where R", for instance, is selected from lower alkyl ($C_{1-5}$ alkyl)), azo (—N=N—), ether (—O—), thioether (—S—), bivalent hydrocarbon groups etc. The chain may be built up of amino acid residues of the α-, -or β-, γ-or ε-type or of the L- or the D-type or mixtures of these. The chain may carry one or more positive and/or negative groups, for instance primary, secondary, tertiary and quaternary ammonium groups, respective carboxy and sulfonate groups. In case L is a peptide chain it may contain from 1-15 amino acid residues or even more. One type of linkers comprises a hydrocarbon chain which (a) is straight branched or cyclic and possibly is interrupted at one or more positions by an oxygen or a nitrogen and/or (b) has one or more carbons that are substituted with an $NR_1R_2$ or an —$OR_3$ group in which $R_{1-3}$ is selected amongst $C_{1-10}$ alkyl. One kind of linker complying with this is a poly(ethylene glycol) linker with formula —$(CH_2CH_2O)_n$—, where n may be an integer 1-10.

Y may be attached to the X and Z moieties at various locations.

In the case of cAMP-dependent protein kinase the optimization of the length of Y has been performed previously with inhibitors of lower affinity incorporating L-arginine residues. [Loog et al., Bioorg. Med. Chem. Lett., 9 (1999) 1447] Structure-activity studies showed that for the conjugate with X=adenosine-5'-carboxylic acid and Z=hexa(L-arginine) the optimal tether Y is 6-aminohexanoic acid [$NH_2(CH2)_n$ (COOH, n=5] The same length of the tether turned out to be optimal for the high-affinity bisubstrate inhibitors of the present invention (Example 2, Table 2).

The conjugates with the highest affinity can be linked to a fluorescent dye and new fluorescent probes with requested properties will be obtained.

Different synthetic methods that were introduced for the preparation of bisubstrate-analog inhibitors are described in the Schemes 1-4.

Scheme 1
Synthesis of the bisubstrate-analog inhibitors, conjugates of Adc and a peptide

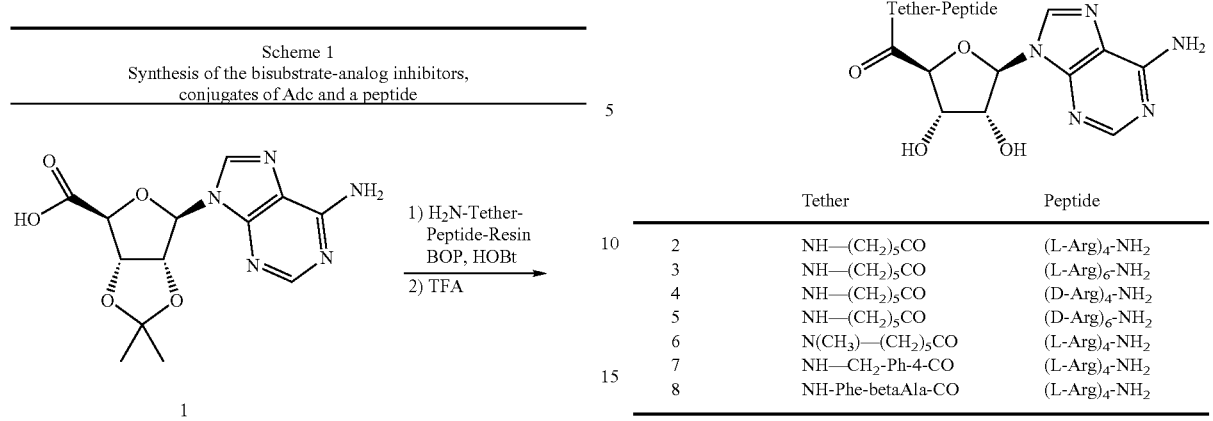

| | Tether | Peptide |
|---|---|---|
| 2 | NH—(CH$_2$)$_5$CO | (L-Arg)$_4$-NH$_2$ |
| 3 | NH—(CH$_2$)$_5$CO | (L-Arg)$_6$-NH$_2$ |
| 4 | NH—(CH$_2$)$_5$CO | (D-Arg)$_4$-NH$_2$ |
| 5 | NH—(CH$_2$)$_5$CO | (D-Arg)$_6$-NH$_2$ |
| 6 | N(CH$_3$)—(CH$_2$)$_5$CO | (L-Arg)$_4$-NH$_2$ |
| 7 | NH—CH$_2$-Ph-4-CO | (L-Arg)$_4$-NH$_2$ |
| 8 | NH-Phe-betaAla-CO | (L-Arg)$_4$-NH$_2$ |

Scheme 2. Synthesis of the bisubstrate-analog inhibitors, conjugates of adenosine and a peptide

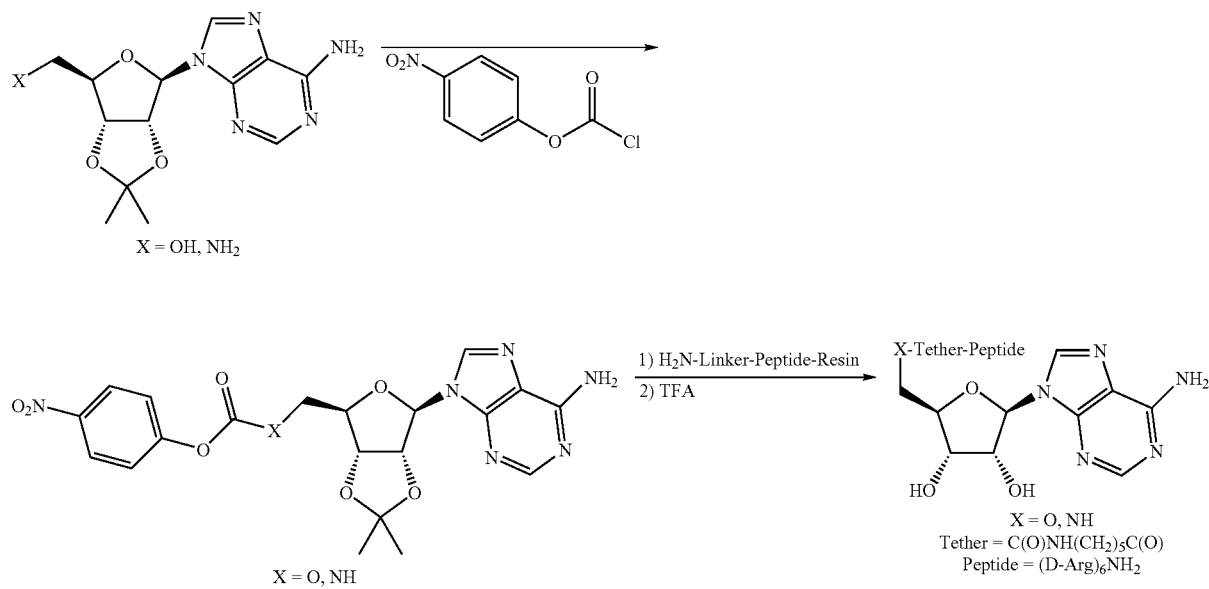

Scheme 3. Synthesis of the bisubstrate-analog inhibitors, conjugates of adenine and a peptide

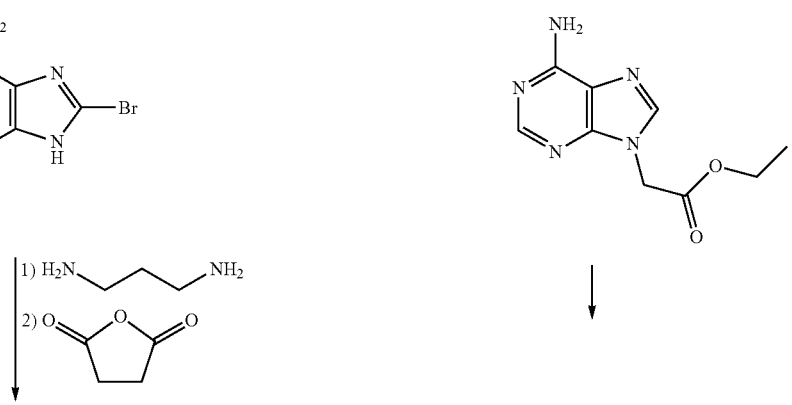

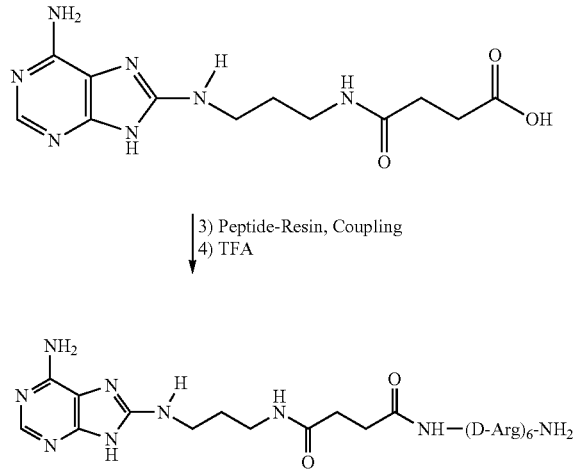

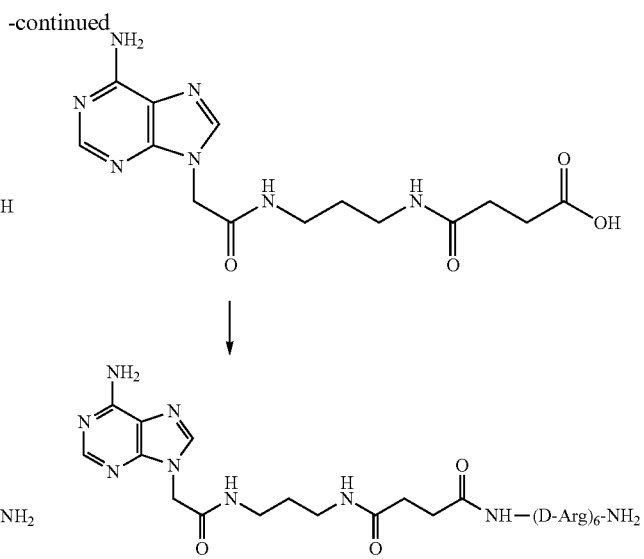

Scheme 4. Synthesis of the bisubstrate-analog inhibitors, conjugates of isoquinolinesulfonamide derivative H9 and a peptide

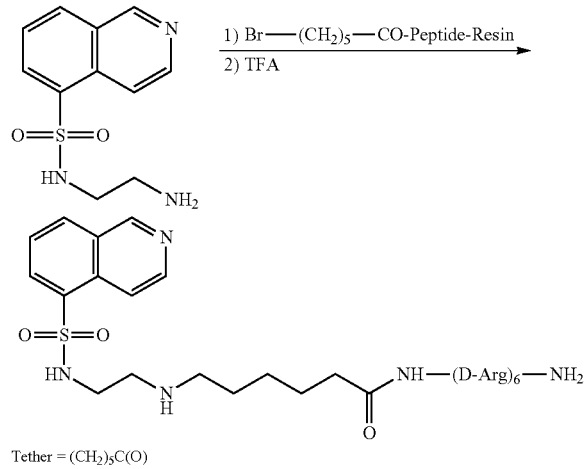

Tether = $(CH_2)_5C(O)$
Peptide = $(D\text{-}Arg)_6NH_2$

Structure-Activity Studies with cAMP-Dependent Protein Kinase (cAPK)

The inhibitory potency of the synthesized conjugates was tested towards cAMP-dependent protein kinase (cAPK), a well characterized representative of basophilic protein kinases. In the case of Adc-peptide conjugates the amidation of peptide C-terminus increased the potency of bisubstrate inhibitors 2-3 fold. This may be caused by the compensation of the positive charge of an arginine residue that participates in a favourable contact with the kinase by the negative charge of the carboxylate group. Substantial modifications in the structure of the tether between adenosine and peptide moieties of conjugates were well tolerated by cAPK (Table 2, compounds 2, 6, 8), while some small structural modifications led to significant decrease of activity.

Variation of the structure of the conjugates also included the connection of adenosine to the C-terminus of the oligoarginine chain and the incorporation of residues of D-arginine.

Inhibitors with peptide moieties connected to the nucleoside part by C- and N-termini had similar affinities in the case of compounds containing peptides with L-amino acid residues, whereas the compound comprising the peptide with D-arginine residues connected via the C-terminus had 500-fold lower activity than the counterpart with N-terminal peptide (5). The bisubstrate character of the inhibitor 5 is supported by the high inhibitory potency of the compound if compared to the submillimolar potencies of the single site-targeted constituents of the conjugate, adenosine and oligo-(D-arginine).

The inhibitory potency of the fluorescent probe ARC-TAMRA, AdcAhx(D-Arg)$_6$-D-Lys(5-TAMRA)-NH$_2$, was also established with the inhibition assay. The obtained IC$_{50}$ value of inhibition 6.2 nM is even lower than that of the corresponding bisubstrate inhibitor AdcAhx(D-Arg)$_6$NH$_2$ (IC$_{50}$=8.3 nM). The result shows that the addition of the linker (D-lysine) and the fluorescent dye (5-TAMRA) to the special position of the biligand inhibitor does not interfere substantially with its binding to the kinase.

Selectivity Study

Selectivity testing was performed (Example 3) for two compounds, 5 and 26, that had revealed the highest inhibitory potency towards cAPK Cα. The panel of kinases included all 52 kinases available for testing. To the best of our knowledge, the selectivity profiling has not been carried out with a wide panel of PK before for bisubstrate-type inhibitors. To make the inhibitory potencies comparable, assays were run at the ATP concentrations which were close to the K$_m$ value of the kinase. The results are presented (Example 3) at 1 µM concentration of the inhibitor as the percent of residual activity of the kinase relative to that in control incubations where the inhibitor was omitted.

The activity profiles of two compounds were mostly similar. Both conjugates inhibited strongly ROCK-II, MSK1, PKBβ, PKBΔph, and PRK2 (residual activity≦3%). Compound 26 inhibited almost completely MAPKAP-K1a/rsk1, p70S6K, and MAPKAP-K1b, while residual activity in the presence of 5 was 7-28% for these kinases. The biggest difference between the two compounds was observed for the inhibition of MAPKAP-K1a/rsk1 where the corresponding values were 0 and 28% for 26 and 5, respectively.

CAMK-1, PKA, PIM2, and PKD1 retained less than 10% of activity in the presence of 26. The significant difference between the two compounds was also found for PKD1 (the residual activities were 54% for 5 and 9% for 26). Checkpoint kinases (CHK1 and CHK2) were both inhibited more strongly by 5 than by 26. Several kinases were weakly inhibited by biligand inhibitors, while some of them were not inhibited at all, e.g., acidophilic kinases represented by casein kinases CK1 and CK2 retained full activity in the presence of 5 as well as 26. As illustrated by data in Table 2, oligo-(D-arginine) containing bifunctional inhibitors were not specific to any particular protein kinase but slowed down the reactions catalyzed by basophilic kinases, especially of the AGC (cAMP dependent, cGMP dependent, and protein kinase C family) and CAMK (calmodulin-dependent protein kinase) groups. Of the 14 PK inhibited by more than 85% by compound 26 at 1 micromolar concentration, 11 kinases belong to the AGC group and 3 kinases to the CAMK group. All these 14 kinases have been reported to be of basophilic type which points to the biligand character of the inhibitors where the inhibitory potency of the conjugates is influenced by binding to both substrate-binding sites of the kinase. The only AGC group kinase that falls out of this selection is PDK, an AGC kinase which expresses badly defined consensus sequences and lacks strong Arg preference at any position.

On the basis of the analysis of the results of the selectivity study of two inhibitors with 52 kinases, previously known substrate consensus sequences and other structural characteristics we have selected 59 protein kinases from the AGC family that are potential binders to the fluorescent probes disclosed in the present invention (Table 1).

TABLE 1

59 kinases from AGC group (classification by [Manning et al., Science 298 (2002) 1912]) which on the basis of the analysis of their substrate consensus sequences and other characteristics are potential binders to the fluorescent probes disclosed in the present invention

| Number | Kinase | Accession | Group | Family | Subfamily |
|---|---|---|---|---|---|
| 1 | AKT1 | SK018 | AGC | AKT | |
| 2 | AKT2 | SK019 | AGC | AKT | |
| 3 | AKT3 | SK020 | AGC | AKT | |
| 4 | DMPK1 | SK111 | AGC | DMPK | GEK |
| 5 | DMPK2 | SK112 | AGC | DMPK | GEK |
| 6 | MRCKb | SK241 | AGC | DMPK | GEK |
| 7 | MRCKa | SK299 | AGC | DMPK | GEK |
| 8 | MRCKps | SK660 | AGC | DMPK | GEK |
| 8 | ROCK2 | SK263 | AGC | DMPK | ROCK |
| 10 | ROCK1 | SK331 | AGC | DMPK | ROCK |
| 11 | CRIK | SK695 | AGC | DMPK | |
| 12 | MAST3 | SK196 | AGC | MAST | |
| 13 | MAST2 | SK216 | AGC | MAST | |
| 14 | MAST1 | SK345 | AGC | MAST | |
| 15 | MASTL | SK455 | AGC | MAST | |
| 16 | MAST4 | SK701 | AGC | MAST | |
| 17 | NDR1 | SK249 | AGC | NDR | |
| 18 | LATS1 | SK441 | AGC | NDR | |
| 19 | LATS2 | SK442 | AGC | NDR | |
| 20 | NDR2 | SK500 | AGC | NDR | |
| 21 | PKACa | SK300 | AGC | PKA | |
| 22 | PKACb | SK301 | AGC | PKA | |
| 23 | PKACg | SK302 | AGC | PKA | |
| 24 | PRKX | SK313 | AGC | PKA | |
| 25 | PRKXps | SK319 | AGC | PKA | |
| 26 | PRKY | SK320 | AGC | PKA | |
| 27 | PKCa | SK303 | AGC | PKC | Alpha |
| 28 | PKCb | SK304 | AGC | PKC | Alpha |
| 29 | PKCg | SK307 | AGC | PKC | Alpha |
| 30 | PKCd | SK305 | AGC | PKC | Delta |
| 31 | PKCt | SK310 | AGC | PKC | Delta |
| 32 | PKCh | SK270 | AGC | PKC | Eta |
| 33 | PKCe | SK306 | AGC | PKC | Eta |
| 34 | PKCi | SK308 | AGC | PKC | Iota |
| 35 | PKCz | SK311 | AGC | PKC | Iota |
| 36 | PKCips | SK711 | AGC | PKC | iota |
| 37 | PKG1 | SK073 | AGC | PKG | |
| 38 | PKG2 | SK075 | AGC | PKG | |
| 39 | PKN1 | SK317 | AGC | PKN | |
| 40 | PKN2 | SK318 | AGC | PKN | |
| 41 | PKN3 | SK511 | AGC | PKN | |
| 42 | MSK1 | SK242 | AGC | RSK | MSK |
| 43 | MSK2 | SK243 | AGC | RSK | MSK |
| 44 | p70S6K | SK265 | AGC | RSK | p70 |
| 45 | p70S6Kb | SK266 | AGC | RSK | p70 |
| 46 | p70S6Kps2 | SK640 | AGC | RSK | p70 |
| 47 | p70S6Kps1 | SK740 | AGC | RSK | p70 |
| 48 | RSK1 | SK336 | AGC | RSK | RSK |
| 49 | RSK2 | SK337 | AGC | RSK | RSK |
| 50 | RSK3 | SK338 | AGC | RSK | RSK |
| 51 | RSK4 | SK518 | AGC | RSK | RSK |
| 52 | SgK494 | SK491 | AGC | RSK | |
| 53 | RSKL2 | SK473 | AGC | RSKL | |
| 54 | RSKL1 | SK517 | AGC | RSKL | |
| 55 | SGK | SK346 | AGC | SGK | |
| 55 | SGK2 | SK523 | AGC | SGK | |
| 56 | SGK3 | SK525 | AGC | SGK | |
| 57 | YANK3 | SK469 | AGC | YANK | |
| 58 | YANK2 | SK481 | AGC | YANK | |
| 59 | YANK1 | SK624 | AGC | YANK | |

Profiling with the 52-kinase selectivity panel (Example 3) reveals strong tendency of the arginine-rich conjugates to inhibit specifically basophilic protein kinases that points to the active participation of both functionary moieties in the formation of the binary complex with the kinase. In addition to the majority of AGC kinases, many kinases of CAMK and STE groups and some kinases not falling into major groups (classification by [Manning et al., Science 298 (2002) 1912]) have also been shown to be basophilic protein kinases [Pinna et al., Biochim. Biophys. Acta. 1314 (1996) 191; Zhu et al., J. Biol. Chem. 280 (2005) 36372]. All these kinases could be targets of fluorescent probes of the present invention and the probes can be used in analytical methods concerning these kinases.

Additionally, the targets of the fluorescent probes of the present invention are different mutated forms of basophilic protein kinases, truncated forms of kinases inactive states of protein kinases, and pseudokinases.

EXPERIMENTAL PART

Abbreviations

Adc—5'-adenosine carboxylic acid or 1-(6-amino-9H-purin-9-yl)-1-deoxy-□-D-ribofuranuronic acid (CAS 3415-09-6);
Ahx—6-aminohexanoic acid;
Arg—arginine;
ARC—adenosine-arginine conjugate;
ATP—adenosine-5'-triphosphate;
Boc—tert-butoxycarbonyl;
cAMP—cyclic adenosine 3',5'-monophosphate;
cAPK—cAMP-dependent protein kinase;
DIC—1,3-diisopropylcarbodiimide;
DIPEA—N,N-diisopropylethylamine;
DMF—dimethylformamide;
DMSO—sulfoxide;
DTT—dithiothreitol
Fmoc—9-fluorenylmethoxycarbonyl;
HOBt—1-hydroxybenzotriazole;

HPLC—high performance liquid chromatography;
Ip: 2',3'-O-isopropylidene;
MALDI TOF MS, matrix assisted laser desorption ionisation time-of-flight mass spectrometry;
NMR—nuclear magnetic resonance;
Pbf—2,2,4,6,7-pentamethyldihydrobenzofuran-5-sulfonyl;
PK—protein kinase;
PKA—cAMP-dependent protein kinase;
RP—reverse phase;
TFA—trifluoroacetic acid;
TLC—thin layer chromatography.

EXAMPLES

Example 1

Synthetic Procedures

Solid Phase Synthesis Procedures

Peptide fragments were prepared by using traditional Fmoc solid-phase peptide synthesis methods on Rink amide MBHA resin (Schemes 1-4). Protected amino acids (3 equivalents) were dissolved in DMF and activated with BOP/HOBt (2.94 eq each) in DMF/N-methylmorpholine. Coupling solutions were added to the resin and shaked for 40-60 min. The completeness of each step was monitored with Kaiser-test, which was followed by deprotection of Fmoc-group by 20% piperidine solution in DMF (20 min). Fmoc-protected linker, 6-Fmoc-aminohexanoic acid, was attached to the peptide part following the same protocol. The N-terminal Fmoc group was removed with 20% piperidine solution in DMF (20 min). Adenosine-5'-carboxylic acid was attached to the resin-bound peptide in the form of its isopropylidene protected derivative (3 equivalents) in DMF and activated with BOP/HOBt (2.94 eq each) in DMF/diisopropylethylamine. The protection groups were removed and the conjugate cleaved from the resin with 2 h treatment with 90% trifluoroacetic acid (5% triisopropylsilane, 5% water). The conjugate was purified with C18 reversed phase HPLC and lyophilized.

Synthesis of the fluorescent probe AdcAhx(D-Arg)$_6$-D-Lys(5-TAMRA)-NH$_2$ (ARC-TAMRA)

AdcAhx(D-Arg)$_6$-D-Lys-C(O)NH$_2$ in the form of its TFA salt (2.5 mg, 1 μl) was dissolved in DMSO. 5-TAMRA, SE (5-Carboxytetramethylrhodamine, succinimidyl ester) (Anaspec; 0.53 mg, 1 μmol) in DMF (50 μl) and DIEA (10 μl) were added. After 3 h reaction the solvents were removed in the freeze dryer and the product, AdcAhx(D-Arg)$_6$-D-Lys(5-TAMRA)-C(O)NH$_2$, purified by HPLC with C18 reversed phase column. MW (MALDI TOF, M+H$^+$)=1870; $\lambda_{max}$ (absorption)=559 nm; $\lambda_{max}$(emission)=582 nm.

Adc-Ahx-(D-Arg$_6$)-[D-Lys(5-TAMRA)]-NH$_2$ has excitation and emission maxima at 559 nm and 582 nm (50 mM HEPES, 200 mM NaCl, 0.5 g/l BSA, 5 mM DTT, 0.05% TWEEN 20, MilliQ water; pH 7.4), respectively. The spectra were recorded on Perkin Elmer fluorescence spectrometer LS 55.

Synthesis of the fluorescent probe AdcAhx(D-Arg$_L$-D-Lys(NBD)-NH$_2$

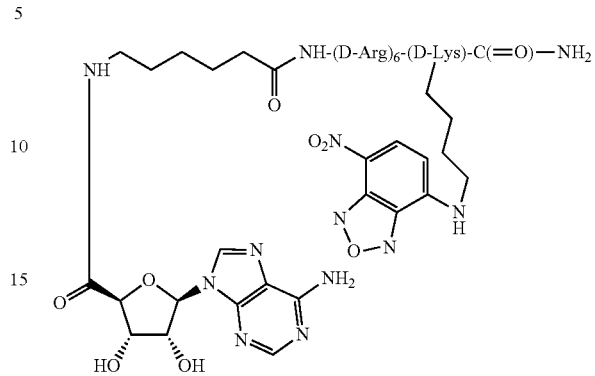

AdcAhx(D-Arg)$_6$-D-Lys-C(O)NH$_2$ in the form of its TFA salt (2.5 mg, 1 mmol) was dissolved in DMSO (100 μl). 4-Fluoro-7-nitrobenzofurazan (NBD-F) (Anaspec; 0.2 mg, 1.0 μmol) in DMF (100 μl) was added. After 3 h reaction at room temperature the solution was put into the freeze-dryer and the solvents were removed. HPLC purification on a C18 reversed phase column with water-ACN gradient gave the product in the form of dark powder. MW (MALDI TOF, M+H$^+$)=1751. $\lambda$(max) at 480 nm in water, $\lambda$(max) at 466 nm in methanol.

Synthesis of the fluorescent probe H9-Hex-(D-Arg)$_6$-D-Lys(5-TAMRA)-C(O)NH$_2$

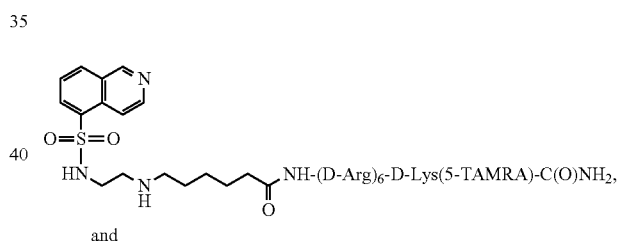

and

Bromohexanoic acid (10 eq) was activated with DIC (5 eq) at 0° C. in DMF and added to the resin [Arg(Pbf)]$_6$Lys(Boc)-[MBHA amide resin]. After 45 min agitation the resin was washed. The resulting alkyl bromide was reacted with 5-isoquinolinesulfonyl ethylenediamine (H9) in DMSO for 12 h at 50° C. Secondary amino group of the resin-bound conjugate was protected with Fmoc-Cl (1 h, room temp; 3 eq., 10 eq. DIEA, DMF). The product was cleaved from the resin and isopropylidene and Boc groups were removed by 2 h treatment with 90% TFA (5% water, 5% diisopropylsilane) to produce
IQS-NH—(CH$_2$)$_2$—N(Fmoc)-(CH$_2$)$_5$C(=O)-(D-Arg)$_6$-D-Lys-NH$_2$. After cleavage from the resin (90% TFA, 5% water, 5% TIS) and purification by reversed phase HPLC (water-ACN gradient, 0.1% TFA) the product was reacted with 5-TAMRA, SE (1 eq.) for 3 h in the mixture of DMF and DMSO (1:1) in the presence of DIEA (5 eq.). After cleavage from the resin (90% TFA, 5% water, 5% TIS) and purification by reversed phase HPLC (water-ACN gradient, 0.1% TFA), the modified peptide H9-Hex-(D-Arg)$_6$-(D-Lys)-NH$_2$ was reacted with 5-TAMRA, SE in DMSO (100 μl) in the presence of DIEA (10 μl) for 3 h at roomt°.

H9-Hex(D-Arg)$_6$-D-Lys(5-TAMRA)-C(O)NH$_2$ was purified with HPLC on a C18 reversed phase column. Dark red powder was obtained after freeze drying; $\lambda_{max}$(absorption)= 559 nm; $\lambda_{max}$(emission)=582 nm.

Example 2

Optimization of the Structure of the Bisubstrate-Analog Inhibitor: Determination of Inhibition Characteristics IC$_{50}$ Towards cAPK Cα

The IC$_{50}$ values of the inhibitors were measured as previously described. [Viht et al., Anal. Biochem. 340 (2005) 165] The inhibitors in various concentrations were incubated at 30° C. in Hepes buffer (50 mM, pH=7.5) containing cAPK Cα (Biaffin AG; about 1 nM), TAMRA-kemptide (10, 30 or 100 μM), ATP (100 μM or 1 mM), magnesium acetate (10 mM) and bovine serum albumin (nhibitr 0.2 mg/mL). ATP was added last to initiate the phosphorylation reaction. At fixed time points, the reaction was stopped by 20-fold dilution with 75 mM phosphoric acid and obtained solutions were analyzed by normal phase TLC (without fluorescence indicator, eluted with 1-butanol/pyridine/acetic acid/water, 15/10/12/12 by volume). The visualization and quantification of the fluorescent spots were carried out by fluorescence imaging. Data were processed with Graphpad Prism software (version 4, GraphPad).

TABLE 2

Values of IC$_{50}$ for the conjugates of oligoarginines and adenosine-5'-carboxylic acid (structures 2-8 from Sheme 1), conjugates of oligoarginines and isoquinoline sulfonamides (25 and 26), fluorescent probe ARC-TAMRA, and some single site-targeted inhibitors of the phosphorylation reaction catalyzed by cAPK Cα

| Compound | Structure | IC$_{50}$ (μM) |
|---|---|---|
| A | AdcAhx(L-Arg)$_6$OH<br>Viht et al., Anal. Biochem. 340 (2005) 165 | 0.40 ± 0.12 |
| 2 | [structure: Adc-Ahx-(L-Arg)$_4$-NH$_2$] | 2.0 ± 0.3 |
| 3 | [structure: Adc-Ahx-(L-Arg)$_6$-NH$_2$] | 0.17 ± 0.04 |
| 4 | [structure: Adc-Ahx-(D-Arg)$_4$-NH$_2$] | 0.33 ± 0.03 |
| 5 | [structure: Adc-Ahx-(D-Arg)$_6$-NH$_2$] | 0.0083 ± 0.0015 |

TABLE 2-continued

Values of IC$_{50}$ for the conjugates of oligoarginines and adenosine-5'-carboxylic acid (structures 2-8 from Sheme 1), conjugates of oligoarginines and isoquinoline sulfonamides (25 and 26), fluorescent probe ARC-TAMRA, and some single site-targeted inhibitors of the phosphorylation reaction catalyzed by cAPK Cα

| Compound | Structure | IC$_{50}$ (μM) |
|---|---|---|
| 6 | 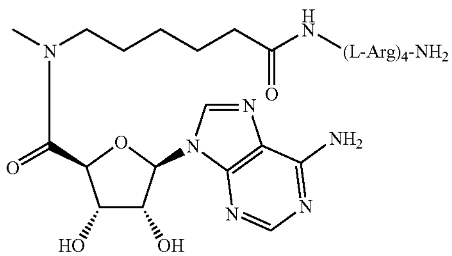 | 2.6 ± 0.6 |
| 7 | 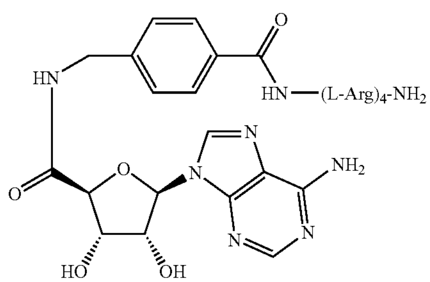 | 23 ± 4 |
| 8 | 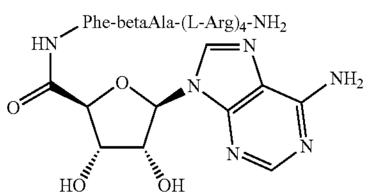 | 3.7 ± 0.3 |
| 25 | 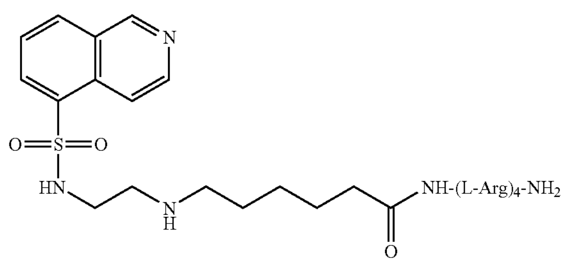 | 0.030 ± 0.007 (0.22 ± 0.03) |
| 26 | 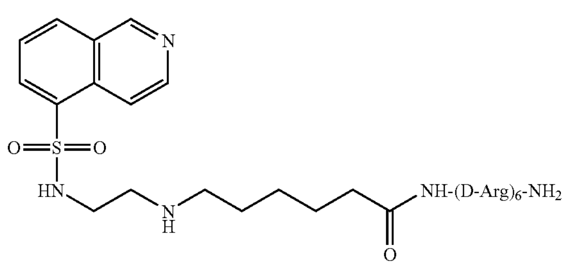 | 0.0053 ± 0.0007 (0.067 ± 0.019) |
| 27 | Ac-(D-Arg)$_6$-D-Lys-NH$_2$ | ~3000 |

TABLE 2-continued

Values of IC$_{50}$ for the conjugates of oligoargininnes and adenosine-5'-carboxylic acid (structures 2-8 from Sheme 1), conjugates of oligoargininnes and isoquinoline sulfonamides (25 and 26), fluorescent probe ARC-TAMRA, and some single site-targeted inhibitors of the phosphorylation reaction catalyzed by cAPK Cα

| Compound | Structure | IC$_{50}$ (µM) |
|---|---|---|
| Ado | (adenosine structure) | 350 ± 40 |
| H89 | (isoquinoline sulfonamide structure with Br) | 0.10 ± 0.02 (0.85 ± 0.09) |
| H9 | (isoquinoline sulfonamide structure) | 3.7 ± 0.3 |
| ARC-TAMRA | AdcAhx(D-Arg)$_6$-D-Lys(5-TAMRA)-NH$_2$ | 0.0062 ± 0.0021 |

IC$_{50}$-s are measured in the presence of 100 µM ATP and 30 µM TAMRA-kemptide.

Example 3

Selectivity of Bisubstrate-Analog Inhibitors of PK

To establish the selectivity of two most potent inhibitors of cAPK (5 and 26, Table 2) towards other kinases their inhibitory effect was determined in a panel of 52 kinases. The assay of protein kinases was performed at 30° C. as described previously [Davies et al., Biochem. J. 351 (2000) 95; Murray et al., Biochem. J. 384 (2004) 477]. The results of the testing are expressed as the % of residual activity of the kinase in the presence of the inhibitor at 1 micromolar concentration.

TABLE 3

Residual activities of protein kinases in the presence of biligand inhibitors AdcAhx(D-Arg)$_6$-NH$_2$, 5, and H9-Hex(D-Arg)$_6$-NH$_2$, 26

| protein kinase | kinase group | ATP (µM) | residual activity[a] (%) compound 5 (1 µM) | compound 26 (1 µM) |
|---|---|---|---|---|
| ROCK-II | AGC | 20 | 0 (±0) | 0 (±0) |
| MAPKAP-K1a/rsk-1 | AGC | 50 | 28 (±7) | 0 (±1) |
| SGK | AGC | 20 | 16 (±0) | 1 (±0) |
| MSK1 | AGC | 20 | 2 (±0) | 1 (±1) |
| PKBΔph | AGC | 5 | 2 (±0) | 2 (±0) |
| P70 S6K | AGC | 20 | 7 (±2) | 2 (±0) |
| MAPKAP-K1b/rsk-2 | AGC | 50 | 12 (±0) | 2 (±0) |
| PRK2 | AGC | 5 | 2 (±1) | 2 (±0) |
| PKBb | AGC | 50 | 3 (±0) | 3 (±0) |
| CAMK-1 | CAMK | 50 | 15 (±2) | 6 (±0) |
| PKA | AGC | 20 | 11 (±7) | 6 (±2) |
| PIM2 | CAMK | 5 | 38 (±3) | 9 (±0) |
| PKD1 | CAMK | 50 | 54 (±8) | 9 (±1) |
| PKCa | AGC | 20 | 31 (±7) | 15 (±5) |
| CHK2 | CAMK | 20 | 14 (±2) | 22 (±5) |
| MST2 | STE | 20 | 77 (±3) | 24 (±0) |
| CHK1 | CAMK | 20 | 16 (±4) | 31 (±1) |
| MNK2 | CAMK | 50 | 99 (±9) | 31 (±3) |
| AMPK | CAMK | 50 | 48 (±6) | 39 (±4) |
| ERK8 | CMGC | 5 | 50 (±9) | 52 (±0) |
| Aurora B | other | 20 | 103 (±5) | 53 (±1) |
| MARK3 | CAMK | 5 | 40 (±3) | 53 (±4) |
| PDK1 | AGC | 20 | 62 (±4) | 56 (±1) |
| NEK7 | other | 20 | 58 (±1) | 56 (±9) |
| PBK | TK | 50 | 88 (±5) | 67 (±4) |
| MNK1 | CAMK | 50 | 102 (±1) | 68 (±9) |
| DYRK1a | CMGC | 50 | 72 (±6) | 69 (±1) |
| MAPKAP-K3 | CAMK | 20 | 67 (±0) | 69 (±8) |
| CSK | TK | 20 | 48 (±9) | 70 (±1) |
| CDK2/cyclin A | CMGC | 20 | 88 (±7) | 73 (±3) |

TABLE 3-continued

Residual activities of protein kinases in the presence of biligand inhibitors AdcAhx(D-Arg)$_6$-NH$_2$, 5, and H9-Hex(D-Arg)$_6$-NH$_2$, 26

| protein kinase | kinase group | ATP (μM) | compound 5 (1 μM) residual activity$^a$ (%) | compound 26 (1 μM) |
|---|---|---|---|---|
| JNK/SAPK1c | CMGC | 20 | 70 (±7) | 75 (±4) |
| PLK1 | other | 5 | 81 (±10) | 76 (±2) |
| SAPK2a/p38 | CMGC | 50 | 79 (±2) | 76 (±7) |
| SAPK2b/p38β2 | CMGC | 20 | 85 (±0) | 80 (±2) |
| MAPKAP-K2 | CAMK | 20 | 85 (±6) | 80 (±2) |
| MKK1 | STE | 5 | 77 (±9) | 84 (±6) |
| IKKb | other | 5 | 94 (±11) | 87 (±1) |
| CK2 | other | 5 | 104 (±9) | 87 (±7) |
| Src | TK | 50 | 84 (±9) | 88 (±4) |
| Lck | TK | 50 | 70 (±3) | 88 (±3) |
| smMLCK | CAMK | 50 | 72 (±0) | 90 (±5) |
| eEF2K | atypical | 5 | 92 (±9) | 91 (±8) |
| JNK3 | CMGC | 50 | 91 (±6) | 92 (±9) |
| SAPK4/p38d | CMGC | 5 | 107 (±1) | 93 (±1) |
| GSK3b | CMGC | 5 | 56 (±4) | 94 (±9) |
| MAPK2/ERK2 | CMGC | 50 | 100 (±3) | 95 (±7) |
| CK1 | CK1 | 20 | 106 (±8) | 97 (±4) |
| PRAK | CAMK | 20 | 89 (±4) | 97 (±8) |
| NEK2a | other | 50 | 82 (±2) | 98 (±6) |
| SAPK3/p38g | CMGC | 5 | 111 (±4) | 99 (±1) |
| SRPK1 | CMGC | 50 | 100 (±3) | 99 (±2) |
| NEK6 | other | 50 | 94 (±8) | 100 (±8) |

Example 4

Characterization of the Complex Between the Fluorescent Probe ARC-TAMRA and the Kinase cAPK Cα

ARC-TAMRA, Adc-Ahx-(D-Arg$_6$)-[D-Lys(5-TAMRA)]-NH$_2$, has excitation and emission maxima at 559 nm and 582 nm (50 mM HEPES, 200 mM NaCl, 0.5 g/l BSA, 5 mM DTT, 0.05% TWEEN 20, MilliQ water; pH 7.4), respectively. The spectra were recorded on Perkin Elmer fluorescence spectrometer LS 55.

The binding of the fluorescent probe ARC-TAMRA to the kinase cAPK Cα (Biaffin) was studied at 10 nM or 2 nM ARC-TAMRA concentration (excitation at 557 nm, slitwidth 10 nm; emission at 585 nm, slitwidth 10 nm, detection of fluorescence polarization).

10 nM solution of ARC-TAMRA in 500 μl of buffer (50 mM HEPES, 200 mM NaCl, 0.5 g/l BSA, 5 mM DTT, 0.05% TWEEN 20, MilliQ water; pH 7.4) was titrated with the solution of kinase cAPK Cα (Biaffin). 1-3 μl quantities of various dilutions of kinase solution were added to 500 μl of 2.0 nM or 10.0 nM solution of ARC-TAMRA, and fluorescence anisotropy was measured after each addition of the kinase solution after 10 min delay time. The change in fluorescence anisotropy was plotted against the kinase concentration [cAPK Cα]. The data were fitted to the equation:

$$A = A_f + (A_b - A_f)\frac{L_t + K_d + R_t - \sqrt{(L_t + K_d + R_t)^2 - 4 \cdot L_t \cdot R_t}}{2 \cdot L_t}$$

where, A is measured anisotropy; $A_f$ is the anisotropy of free ARC-TAMRA; $A_b$ is the anisotropy of bound ARC-TAMRA; $L_T$ is the concentration of ARC-TAMRA added, 10 nM; $R_T$ is the total concentration of active kinase (cAPK Cα).

$K_d$ value of 1.0 nM was calculated with 10 nM of ARC-TAMRA (FIGS. 1 and 2).

$K_d$ value of 1.1 nM was calculated with 2 nM of ARC-TAMRA (FIG. 2).

Example 5

Competition Experiments for Determination of the Binding Constants of Inhibitors A complex was created between 10 nM of ARC-TAMRA and 10 nM of cAPK Cα in 0.500 ml of buffer (50 mM HEPES, 200 mM NaCl, 0.5 g/l BSA, 5 mM DTT, 0.05% TWEEN 20, MilliQ water; pH 7.4). Different compounds were screened for binding to cAPK Cα against fixed concentrations of ARC-TAMRA and cAPK Cα (FIG. 4). 1-3 μl quantities of various dilutions of the solution of the inhibitor were added to 500 μl solution of ARC-TAMRA complex with the kinase and fluorescence anisotropy was measured after each addition of the kinase solution after 10 min delay time.

The following values of IC$_{50}$ and K$_i$ were obtained for competitive binding of inhibitors to the ARC-TAMRA-kinase complex:

| Inhibitor | IC$_{50}$ | K$_i$ |
|---|---|---|
| L-ARC | 1.3 μM | 110 nM |
| D-ARC | 35 nM | 2.5 nM |
| H89 | 180 nM | 15 nM |
| PKI (5-24) | 140 μM | 12 μM |

Abbreviations for the compounds: N-(2-[p-bromocinnamylamino-]ethyl)-5-isoquinoline-sulfonamide (H89); AdcAhx (L-Arg)$_6$-NH$_2$ (L-ARC); AdcAhx(D-Arg)$_6$-NH$_2$ (D-ARC); PKI peptide (5-24).

Binding affinity constants (K$_i$ values) of inhibitors were calculated [Nikolovska-Coleska et al., Anal. Biochem. 332 (2004) 261] according to the relationship $$K_i = [I]_{50}/([L]_{50}/K_d + [P]_0/K_d + 1),$$

where [I]$_{50}$ is the concentration of the free inhibitor at 50% inhibition, [L]$_{50}$ is the concentration of the free labeled ligand at 50% inhibition, [P]$_0$ is the concentration of the free protein at 0% inhibition, and K$_d$ is the dissociation constant of the protein-ligand complex.

Very similar Ki values were obtained for the same inhibitors in the conditions were the complex was created at lower concentrations of the interacting partners, between 2 nM ARC-TAMRA and 5 nM cAPK Cα.

Example 6

Determination of the Concentration of the Active Form of the Kinase

ARC-TAMRA, Adc-Ahx-(D-Arg$_6$)-[D-Lys(5-TAMRA)]—NH$_2$, was used as the fluorescence probe: excitation at 558 nm (bandwidth 10 nm) and emission at 585 nm (bandwidth 10 nm): 50 mM HEPES, 200 mM NaCl, 0.5 g/l BSA, 5 mM DTT, 0.05% TWEEN 20, MilliQ water; pH 7.4. The spectra were recorded on Perkin Elmer fluorescence spectrometer LS 55.

10 nM solution of ARC-TAMRA in 500 μl of buffer (50 mM HEPES, 200 mM NaCl, 0.5 g/l BSA, 5 mM DTT, 0.05% TWEEN 20, MilliQ water; pH 7.4) was titrated with the solution of kinase cAPK Cα (Biaffin). 1-3 μl quantities of various dilutions of kinase solution were added to 500 μl of 2.0 nM or 10.0 nM solution of ARC-TAMRA, and fluorescence anisotropy was measured after each addition of the kinase solution after 10 min delay time. The change in fluorescence anisotropy was plotted (FIG. 3) against the kinase concentration [cAPK Cα]. The fraction of the active (binding) form of the kinase in solution, k, was calculated by the application of nonlinear regression analysis to the relationship [Data were processed with Graphpad Prism software (version 4, GraphPad)]:

$$A = A_f + (A_b - A_f)\frac{L_t + K_d + k \cdot R_t - \sqrt{(L_t + K_d + k \cdot R_t)^2 - 4 \cdot L_t \cdot k \cdot R_t}}{2 \cdot L_t}$$

where A is the measured anisotropy; $A_f$ is the anisotropy of free ARC-TAMRA; $A_b$ is the anisotropy of bound ARC-TAMRA; $L_T$ is the concentration of ARC-TAMRA added, 10 nM; $R_T$ is the total concentration of active kinase (cAPK Cα); Kd is the dissociation constant of the reaction between ARC-TAMRA and cAPK Cα (Kd=1.0 nM).

The obtained k value (FIG. 3) of 0.317 shows that 31.7% of the nominal kinase is in the active (binding to the probe) form in this sample of kinase.

Example 7

High-Throughput Binding Assay for Inhibitors of the Kinase cAPK Cα

The high sensitivity of fluorescence platereader PHERAstar (BMG LABTECH) enabled the realization of displacement experiments at 1 nM concentration of the fluorescent probe ARC-TAMRA, Adc-Ahx-(D-Arg$_6$-[D-Lys(5-TAMRA)]-NH$_2$. Corning 384 well Low Volume NIBS microplates (20 μl or 30 μl reaction volumes) were used for assays. Due to the polar and charged character of the fluorescent probe the selection of the well material of microplate is of great importance and specially designed coatings for fluorescence measurements with polar peptides and proteins are better suited than ordinary glass or polystyrene based well materials. The application of latter materials may lead to adsorption of the probes of the present inventions to the surface of the well of the microtiter plate and misrepresentation of results of the measurements.

Characterization of the Fluorescent Probe

Titrations of 2 nM and 20 nM ARC-TAMRA solutions were performed with cAPK C☐. 2-fold serial dilutions of the kinase were used leading to concentrations of the kinase between 100 nM and 0.05 nM and 20 μl reaction volumes on a 384-well microtiter plate. Before the measurement of fluorescence anisotropies the plate was rotated (400 rpm) for 10 minutes at 30° C. Optical conditions for the measurements were set as the following: 540 nm excitation and 590 nm emission (20 nm bandpass filters). To find the value of Kd, titration curves were analyzed by a scientific curve-fitting program, e.g., GraphPad Prism 4.03, with nonlinear regression, using the function below:

$$A = A_f + (A_b - A_f)\frac{L_t + K_d + k \cdot R_t - \sqrt{(L_t + K_d + k \cdot R_t)^2 - 4 \cdot L_t \cdot k \cdot R_t}}{2 \cdot L_t},$$

where A is measured anisotropy, Af—anisotropy value for free ARC-Photo, Ab—anisotropy value for bound ARC-Photo, Lt—total concentration of ARC-Photo, Rt—nominal total concentration of enzyme, k—concentration of active enzyme divided by nominal concentration of enzyme, Kd—dissociation constant for ARC-Photo complex with enzyme. Kd value of 0.4 was determined for the complex (FIG. 5).

Determination of the Inhibition Constants ($K_i$)

To determine the inhibition constant ($K_i$), 3-fold serial dilutions of a given inhibitor are performed analogously as for titration experiments. Before the measurement of fluorescence anisotropies the plate is rotated (400 rpm) for 10 minutes at 30° C. $K_i$ values of 13 nM for ATP-competitive inhibitor H89, 0.5 nM for substrate protein-competitive inhibitor RIIa (regulatory subunit of cAPK), 21 nM for bisubstrate inhibitor AdcAhx(L-Arg)$_6$-NH$_2$ and 1.1 nM for bisubstrate inhibitor AdcAhx(D-Arg)$_6$-NH$_2$ were determined (FIG. 6).

The obtained $K_i$ values for competitive binding are in good accord with the inhibitory constants for the same compounds of the phosphorylation reaction catalyzed by cAPK Cα (Example 2) and inhibitory constants determined with the same fluorescent probe with a fluorescence spectrometer in a 0.5 ml cell (Example 5).

Example 8

Characterization of the Complex Between the Fluorescent Probe ARC-TAMRA and the Rho-Associated Kinase ROCK II and Determination of the Inhibition Constants for Inhibitors Experiments were performed in the wells of 384-well microtiter plates and with the measurements of fluorescence anisotropy with the platereader PHERAStar according to the protocols described in the Example 7. The titration of the fluorescent probe ARC-TAMRA with the kinase ROCK II enabled the determination of dissociation constant Kd of the complex between ARC-TAMRA and the kinase as of 4 nM (FIG. 7).

The displacement of the fluorescent probe ARC-TAMRA from the complex with the kinase (formed between 2 nM of ARC-Photo and 15 nM of ROCK II) by different inhibitors of ROCK enabled the characterization of the inhibitors with $K_i$ values of 45 nM, 40 nM, and 5 nM for H89, Y-27632, and L-ARC, respectively (FIG. 8).

Similar results were obtained with the application of the other Rho-associated kinase ROCK I, having high structural similarity to ROCK II.

The invention claimed is:

1. A fluorescent probe for a protein kinase selected from the group consisting of:

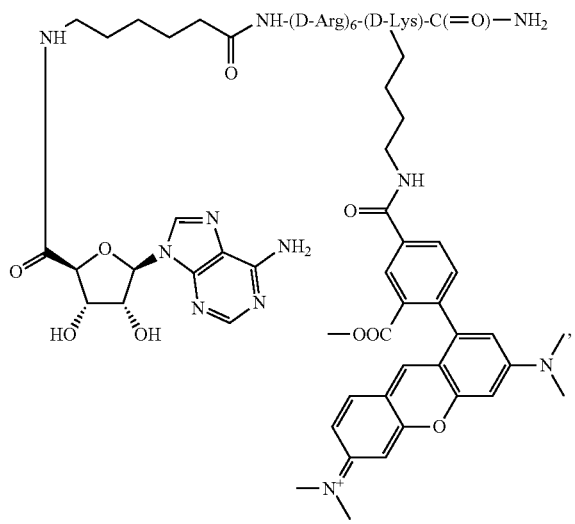

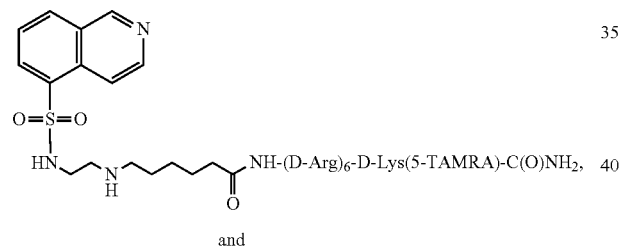

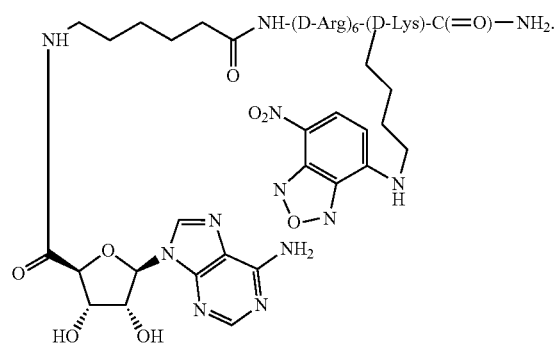

2. A kit comprising a fluorescent probe of claim 1.

3. A bisubstrate-analog inhibitor of a basophilic protein kinase selected from the group consisting of:

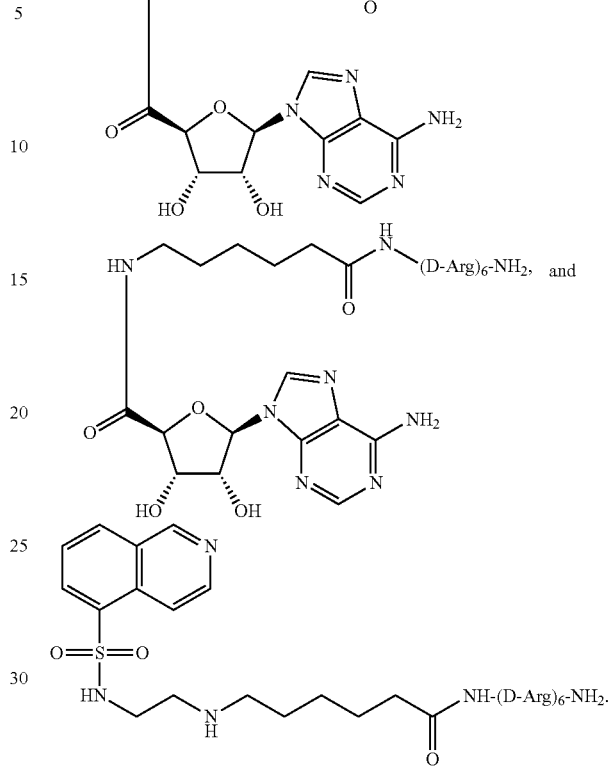

4. A method for determining the fraction of an active binding form of a protein kinase in a sample containing a fluorescent probe of claim 1:
   (a) determining the Kd of a complex of a fluorescent probe of claim 1 and the protein kinase;
   (b) contacting a solution of the protein kinase at various concentration dilutions with a solution of the fluorescent probe to form a sample and measuring the fluorescence anisotropy of each sample after each addition of the protein kinase solution to the sample;
   (c) plotting changes in the fluorescence anisotropy measured in step (b) for each addition against the concentration of the added protein kinase in the sample;
   (d) calculating the fraction of the active binding form of the protein kinase in the sample, k, by application of non-linear regression analysis according to:

$$A = A_f + (A_b - A_f)\frac{L_t + K_d + k \cdot R_t - \sqrt{(L_t + K_d + k \cdot R_t)^2 - 4 \cdot L_t \cdot k \cdot R_t}}{2 \cdot L_t},$$

wherein A is the measured anisotropy of the sample; $A_f$ is the anisotropy of free fluorescent probe in the sample; $A_b$ is the anisotropy of bound fluorescent probe in the complex in the sample; $L_T$ is the concentration of fluorescent probe added to the sample; $R_t$ is the total concentration of the protein kinase in the sample; and Kd is the dissociation constant of the complex of the fluorescent probe and the protein kinase.

5. The method according to claim 4 wherein the fluorescent signal is measured as a shift in fluorescence polarization of the probe.

6. The method according to claim 4 wherein the method is performed on a multi-well plate.

7. The method according to claim 4 wherein the protein kinase is a basophilic protein kinase.

8. The method according to claim 7 wherein the basophilic protein kinase is cAMP-dependent protein kinase.

9. The method according to claim 7 wherein the basophilic protein kinase is Rho-associated kinase (ROCK).

10. An assay for identifying a protein kinase inhibitor by displacement of a fluorescent probe of claim 1 from a complex of a protein kinase and the fluorescent probe by a potential inhibitor compound comprising the steps of:
   (a) contacting a fluorescent probe of claim 1 with the protein kinase to form a complex and measuring a fluorescence signal of the complex;
   (b) contacting the complex of step (a) with a potential inhibitor compound at a concentration to form a mixture;
   (c) measuring a fluorescence signal of the fluorescent probe in the mixture; and
   (d) comparing the fluorescence signals from step (a) and step (c), wherein a difference in the fluorescence signals indicates that the potential inhibitor compound is an inhibitor of the protein kinase at the concentration of the potential inhibitor compound.

11. A method for determining the Kd of a protein kinase inhibitor by displacement of a fluorescent probe of claim 1 from a complex of a protein kinase and the fluorescent probe by an inhibitor compound comprising the steps of:
   (a) contacting a fluorescent probe of claim 1 with the protein kinase to form a complex and measuring a fluorescence signal of the complex;
   (b) contacting the complex with a series of different concentrations of the inhibitor compound and measuring a fluorescence signal at each concentration of the inhibitor compound;
   (c) making a graph of the fluorescent signal corresponding to the concentration of the inhibitor compound measured in step (b); and
   (d) calculating the Kd of the inhibitor compound from the graph of step (c) where in the Kd is the dissociation constant of the inhibitor from the protein kinase.

12. The method according to claim 11 wherein the signal is measured as a shift in fluorescence polarization of the fluorescent probe.

13. The method according to claim 11 wherein the protein kinase is a basophilic protein kinase.

14. The method according to claim 11 wherein the protein kinase is cAMP-dependent protein kinase.

15. The method according to claim 11 wherein the protein kinase is Rho-associated kinase (ROCK).

16. The method according to claim 11 wherein the method is performed on a multi-well plate.

* * * * *